(12) United States Patent
Derby et al.

(10) Patent No.: US 9,380,784 B2
(45) Date of Patent: Jul. 5, 2016

(54) ANTIMICROBIAL COMPOSITIONS AND METHODS OF USE

(76) Inventors: Charles Derby, Decatur, GA (US); Binghe Wang, Marietta, GA (US); Phang C. Tai, Atlanta, GA (US); Ko-Chun Ko, Atlanta, GA (US); Michiya Kamio, Tokyo (JP)

( * ) Notice: Subject to any disclaimer, the term of this patent is extended or adjusted under 35 U.S.C. 154(b) by 936 days.

(21) Appl. No.: 13/055,221

(22) PCT Filed: Jul. 27, 2009

(86) PCT No.: PCT/US2009/051862
§ 371 (c)(1),
(2), (4) Date: Mar. 22, 2011

(87) PCT Pub. No.: WO2010/011998
PCT Pub. Date: Jan. 28, 2010

(65) Prior Publication Data
US 2011/0165261 A1    Jul. 7, 2011

Related U.S. Application Data

(60) Provisional application No. 61/083,790, filed on Jul. 25, 2008.

(51) Int. Cl.
A01N 59/00 (2006.01)
A01P 1/00 (2006.01)
A61P 31/00 (2006.01)
A61K 31/19 (2006.01)
A61K 33/40 (2006.01)
A01N 37/00 (2006.01)

(52) U.S. Cl.
CPC ...................................... A01N 59/00 (2013.01)

(58) Field of Classification Search
None
See application file for complete search history.

(56) References Cited

U.S. PATENT DOCUMENTS

| | | | |
|---|---|---|---|
| 4,363,815 A | 12/1982 | Yu et al. | |
| 5,437,868 A * | 8/1995 | Oakes et al. | 424/405 |
| 5,621,006 A | 4/1997 | Yu et al. | |
| 7,329,517 B2 | 2/2008 | Johnson et al. | |
| 2003/0077301 A1 | 4/2003 | Maibach et al. | |
| 2004/0214215 A1 | 10/2004 | Yu et al. | |
| 2006/0252707 A1 | 11/2006 | Derby et al. | |

FOREIGN PATENT DOCUMENTS

| CN | 101169423 A * | 4/2008 |
|---|---|---|
| CN | 101221187 | 7/2008 |
| WO | WO 93/04216 | 3/1993 |

OTHER PUBLICATIONS

Lukasheva et al., "L-Lysine alpha-Oxidase: Physicochemical and Biological Properties" Biochemistry (Moscow), (2002), vol. 67, No. 10, pp. 1152-1158.*
Australian Patent Application No. 2009273804, Antimicrobial Compositions and Methods of Use, National Stage Entry of PCT/US2009/051862, filed Jul. 27, 2009, Claiming priority to U.S. Appl. No. 61/083,790, filed Jul. 25, 2008.
Australian Patent Application No. 2009273804, Office Action dated Aug. 16, 2013.
Canadian Patent Application No. 2730343, Antimicrobial Compositions and Methods of Use, National Stage Entry of PCT/US2009/051862, filed Jul. 27, 2009, Claiming priority to U.S. Appl. No. 61/083,790, filed Jul. 25, 2008.
European Patent Application No. 09 801 118.2, Antimicrobial Compositions and Methods of Use, National Stage Entry of PCT/US2009/051862, filed Jul. 27, 2009, Claiming priority to U.S. Appl. No. 61/083,790, filed Jul. 25, 2008.
Japanese Patent Application No. 2011-520249, Antimicrobial Compositions and Methods of Use, National Stage Entry of PCT/US2009/051862, filed Jul. 27, 2009, Claiming priority to U.S. Appl. No. 61/083,790, filed Jul. 25, 2008.
Japanese Patent Application No. 2011-520249, Office Action dated Dec. 11, 2012.
Japanese Patent Application No. 2011-520249, Response to Office Action, dated Apr. 21, 2013.
Japanese Patent Application No. 2011-520249, Notice of Allowance, dated Jun. 17, 2013.
Korean Patent Application No. 2011-7004366, Antimicrobial Compositions and Methods of Use, National Stage Entry of PCT/US2009/051862, filed Jul. 27, 2009, Claiming priority to U.S. Appl. No. 61/083,790, filed Jul. 25, 2008.
Barsby T., "Drug Discovery and Sea Hares: Bigger is Better," Trends in Biotechnology, vol. 24 No. 1, (2006).
Kamio et al., "The Chemistry of Escapin: Identification and Quanitification of the Components in the Complex Mixture Generated by an L-Amino Acid Oxidase in the Defensive Secretion of teh Sea Snail *Aplysia californica*," Chem. Eur. J., 15, 1597-1603 (2009).
Ko et al., "Identification of Patent Bactericidal Compounds produced by Escapin, an L-Amino Acid Oxidase in the Ink of the Sea Hare *Aplysia californica*," Antimicrobial Agents and Chemotherapy, Dec., 4455-4462 (2008).
Altschul et al., "Gapped BLAST and PSI-BLAST: A New Generation of Protein Database Search Programs," Nucleic Acids Res., 25(27):3389-3402 (1997).
Annex et al., "Growth Factor-Induced Therapeutic Angiogenesis in the Heart: Protein Therapy," Cardiovascular Research, 65(3):649-655 (2005).
Ardelt et al., "Estradiol Regulates Angiopoietin-1 mRNA Expression Through Estrogen Receptor-α in a Rodent Experimental Stroke Model," Stroke, 36:337-341 (2005).
Auerbach et al., "Angiogenesis Assays: A Critical Overview," Clinical Chemistry, 49:32-40 (2003).

(Continued)

Primary Examiner — Abigail Fisher
Assistant Examiner — Daniel Branson
(74) Attorney, Agent, or Firm — FisherBroyles, LLP; Richard S. Echler

(57) ABSTRACT

Disclosed herein are antimicrobial compositions, kits, and articles of manufacture. Further disclosed herein are methods for treating surfaces, including tissue, inter alia, wounds, with the disclosed compositions.

31 Claims, 6 Drawing Sheets

(56) References Cited

OTHER PUBLICATIONS

Barany et al., "Solid-phase Peptide Synthesis: A Silver Anniversary Report, " *Int. J. Peptide Protein Res.*, 30(6):705-739 (1987).
Bartlett et al., "Molecular Recognition in Chemical and Biological Problems; Cavet: A Program to Facilitate the Structure-Derived Design of Biologically Active Molecules," *Special Pub., Royal Chem. Soc.*, 78:182-196 (1989).
Bohm, "The Computer Program LUDI: A New Method for the De Novo Design of Enzyme Inhibitors," *J. Comuter-Aided. Molec. Design*, 6(1):61-78 (1992).
Bussolino, et al., "Molecular mechanisms of blood vessel formation," *Trends Biochem Sci.* 22(7):251-256 (1997).
Carano et al., "Angiogenesis and Bone Repair," *Drug Discovery Today*, 8(21):980-989 (2003).
Carvalho et al., "The Role of Angiogenesis in a Murine Tibial Model of Distraction Osteogenesis," *Bone*, 34:849-861 (2004).
Chanteau et al., "Synthesis of Anthropomorphic Molecules: The NanoPutians," *J. Org. Chem.*, 68:8750-8766(2003).
Cohen et al., "Molecular Modeling Software and Methods for Medicinal Chemistry," *J. Med. Chem.*, 33(3):883-894 (1990).
Daar, "Perspective: Emerging Resistance Profiles of Newly Approved Antiretroviral Drugs," *Topics in HIV Medicine*, 16(4):110-116 (2008).
Dean, "Recent Advances in Drug Design Methods: Where Will They Lead?" *BioEssays*, 16(9):683-687 (1994).
Fachinger et al., "Functional Interaction of Vascular Endothelial-Protein-Tyrosine Phosphatase with the Angiopoietin Receptor Tie-2," *Oncogene*, 18:5948-5953 (1999).
Flower, "Modelling G-Protein-Coupled Receptors for Drug Design," *Biochimica et Biophysica Acta*, 1422:207-234 (1999).
Folkman, J., "Tumor angiogenesis," *The Molecular Basis of Cancer* (eds. Mendelsohn, J., Howley, P. M., Israel, M. A. & Liotta, L. A.) 206-232 (1995).
Gaits et al., "Increase in Receptor-like Protein Tyrosine Phosphatase Activity and Express Level on Density-Dependent Growth Arrest of Endothelial Cells," *Biochem J.*, 311:97-103 (1995).
Goodford, "A Computational Procedure for Determining Energetically Favorable Binding Sites on Biologically Important Macromolecules," *J. Med. Chem.*, 28(7):849-57 (1985).
Goodsell et al., "Automated Docking of Substrates to Proteins by Simulated Annealing," *Proteins Struct. Funct. Genet.* 8:195-202 (1990).
Harder et al., "Characterization and Kinetic Analysis of the Intracellular Domain of Human Protein Tyrosine Phosphatase β (HPTPβ) Using Synthetic Phosphopeptides," *Biochem. J.*, 296:395-401 (1994).
Henikoff et al., "Amino Acid Substitution Matrices from Protein Blocks," *Proc. Natl. Acad. Sci. USA* 89:10915-10919 (1992).
Hopkins et al., "Inhibitors of Kinesin Activity from Structure-Based Computer Screening," *Biochemistry*, 39:2805-2814 (2000).
Huang et al., "HCPTPA, a Protein Tyrosine Phosphatase that Regulates Vascular Endothelial Growth Factor Receptor-Mediated Signal Transduction and Biological Activity," *J. Biol. Chem.*, 53:38183-38188 (1999).
Itoh et al., "Purification and Characterization of the Catalytic Domains of the Human Receptor-Linked Protein Tyrosine Phosphatases HPTPβ, Leukocyte Common Antigen (LCA), and Leukocyte Common Antigen-Related Molecule (LAR)," *Journal of Biological Chemistry*, 267(17):12356-12363 (1992).
Jones et al., "Development and Validation of a Genetic Algorithm for Flexible Docking," *J. Mol. Biol.*, 267:727-748 (1997).
Jones et al., "Molecular Recognition of Receptor Sites Using a Genetic Algorithm with a Description of Desolvation," *J. Mol. Biol.*, 245:43-53 (1995).
Keen, "Radioligand Binding Methods for Membrane Preparations and Intact cells," *Methods in Molecular Biology*, 83:*Receptor Signal Transduction Protocols*, edited Humana Press Inc., Totoway N.J. (1997).
Köhler et al., "Continuous Cultures of Fused Cells Secreting Antibody of Predefined Specificity," *Biotechnology*, 24:524-526 (1992).

Krueger et al., "Structural Diversity and evolution of Human Receptor-Like Protein Tyrosine Phosphatases," *The EMBO Journal*, 9(10):3241-3252 (1990).
Kugathasan et al., "Role of Angiopoietin-1 in Experimental and Human Pulmonary Arterial Hpertension," *Chest*, 128:633-642 (2005).
Kuntz et al., "A Geometric Approach to Macromolecule—Ligand Interactions," *J. Mol. Biol.* 161:269-288 (1982).
Lin et al., "Inhibition of Tumor Angiogenesis Using a Soluble Receptor Establishes a Role for Tie2 in Pathologic Vascular Growth," *J. Clinical Invest.*,100(8):2072-2078 (1997).
Ma et al., "RNase Protection Assay," *Methods*, 10(3):273-8 (1996).
Martin, "3D Database Searching in Drug Design," *J. of Medicinal Chemistry*, 35(12):2145-2154 (1992).
Meadows, "Keeping Up with Drug Safety Information," 2006: FDA Consumer Magazine: http://www.fda.gov/fdac/features/2006/306_druasafety.html, accessed Mar. 17, 2008.
Merrifield, "Solid Phase Peptide Synthesism. I. The Synthesis of a Tetrapeptide," *J. Am. Chem. Soc.*, 85:2149-2154 (1963).
Miranker et al., "Functionality Maps of Binding Sites: A Multiple Copy Simultaneous Search Method," *Proteins: Struc. Func. And Genectics*, 11(1):29-34 (1991).
Navaza, "AMoRe: An Automated Package for Molecular Replacement," *J. Acta Cryst.* A50:157-163 (1994).
Nguyen et al., "Cellular Interactions in Vascular Growth and Differentiation," *Int. Rev. Cytol.*, 204:1-48 (2001).
Nishibata et al., "Automatic Creation of Drug Candidate Structures Based on Receptor Structure. Starting Point for Artificial Lead Generation," *Tetrahedron*, 47(43):8985-8990 (1991).
O'Reilly, "Angiostatin: a novel angiogenesis inhibitor that mediates the suppression of metastases by a Lewis lung carcinoma," *Cell*, 79(2):315-28 (1994).
O'Reilly, "Endostatin: an endogenous inhibitor of angiogenesis and tumor growth," *Cell*, 88(2):277-85 (1997).
Rarey et al., "A Fast Flexible Docking Method Using an Incremental Construction Algorithm," *J. Mol. Biol.*, 261:470-489 (1996).
Riechmann et al., "Reshaping Human Antibodies for Therapy," *Nature*, 332:323-327 (1988).
Saliba, "Heparin in the Treatment of Burns: A Review," May 2001; Burn 27(4):349-358; full text edition, pp. 1-16.
Schöneberg et al., "Structural basis of G protein-coupled receptor function," *Molecular and Cellular Endocrinology*, 151:181-193 (1999).
Sexton, "Recent advances in our understanding of peptide hormone receptors and RAMPS," *Current Opinion in Drug Discovery and Development*, 2(5):440-448 (1999).
Shiojima et al., "Disruption of Coordinated Cardiac Hypertrophy and Angiogenesis Contributes to the Transition to Heart Failure," *Journal of Clinical Invest.*, 115(8):2108-2118 (2005).
Shoichet et al., "Lead Discovery Using Molecular Docking," *Chem. Biology*, 6:439-446 (2002).
Siddiqui et al., "Combination of angiopoietin-1 and vascular endothelial growth factor gene therapy enhances arteriogenesis in the ischemic myocardium," *Biochem. Biophys. Res. Comm.*, 310:1002-1009 (2003).
Simons, "Angiogenesis: Where Do We Stand Now?," *Circulation*, 111:1556-1566 (2005).
Simons et al., "Clinical Trials in Coronary Angiogenesis," *Circulation*, 102:73-86 (2000).
Stal et al., "Detailed Analysis of Scoring Functions for Virtual Screening," *J. Med. Chem.*, 44:1035-1042 (2001).
Stetler-Stevenson, "The Role of Matrix Metalloproteinases in Tumor Invasion, Metastasis, and Angiogenesis," *Surg. Oncol. Clin. N. Am.*, 10(2):383-392 (2001).
Suggitt et al., "50 Years of Preclinical Anticancer Drug Screening: Empirical to Target-Drive Approaches," *Clinical Cancer Research*, 11:971-981 (2005).
Suri et al., "Increased Vascularization in Mice Overexpressing Angiopoietin-1," *Science*, 282:468-471 (1998).
Takahashi et al.,"Adenoviral-Delivered Angiopoietin-1 Reduces the Infarction and Attenuates the Progression of Cardiace Dysfunction in the Rate Model of Acute Myocardial Infarction," *Molecular Therapy*, 8(4):584-592 (2003).

(56) References Cited

OTHER PUBLICATIONS

Teischer, "Potentiation of cytotoxic cancer therapies by TNP-470 alone and with other anti-angiogenic agents," *Int. J. Cancer*, 57(6)920-925 (1994).

Thurston, "Complimentary Actions of VEGF and Angiopoietin-1 on Blood Vessel Growth and Leakage," *J. Anat.*, 200:575-580 (2002).

Thurston et al., "Angiopoietin-1 Protects the Adult Vasculature Against Plasma Leakage," *Nature Medicine*, 6(4):460-463 (2000).

Vailhe et al., "In Vitro Models of Vasculogenesis and Angiogenesis," *Laboratory Investigation*, 81:439-452 (2001).

Wang et al., "Expressions and Characterization of Wild Type, Truncated, and Mutant Forms of the Intracellular Region of the Receptor-Like Protein Tyrosine Phosphatase HPTPβ," *J. of Bio. Chem.*, 267(23):16696-16702 (1992).

Weidner, "Tumor Angiogenesis and Metastasis Correlation in Invasive Breast Carcinoma," *New Eng. J. Med.*, 324(1):108 (1991).

Whitaker et al., "Vascular Endothelial Growth Factor Receptor-2 and Neuropilin-1 Form a Receptor Complex That is Responsible for the Differential Signaling Potency of $VEGF_{165}$ and $VEGF_{121}$," *Journal of Biological Chemistry*, 276(27):25520-25531 (2001).

Wright et al., "Protein-Tyrosine Phosphatases in the Vessel Wall Differential Expression After Actue Arterial Injury," *Arterioscler Thromb. Vasc.*, 1189-1198 (2000).

Yancopoulos et al., "Vascular-Specific Growth Factors and Blood Vessel Formation," *Nature*, 407(6801):242-248 (2000).

Zhang et al., "Vascular Endothelial Growth Factor and Angiopoietins in Focal Cerebral Ischemia," *Trends Cardiovascular Med.*, 12(2):62-66 (2002).

Collaborative Computational Project, No. 4, "The CCP4 Suite: Programs for Protein Crystallography," *Acta Cryst.*, D50:760-763 (1994).

Extended European Search Report for co-pending European Patent Application 09 801 118.2 dated May 27, 2014.

Abstract cited in Extended European Search Report as document D1.
Abstract cited in Extended European Search Report as document D2.
Abstract cited in Extended European Search Report as document D3.
Abstract cited in Extended European Search Report as document D4.
Abstract cited in Extended European Search Report as document D5.
Abstract cited in Extended European Search Report as document D6.

Gomez D. et al. "A novel type of lysine oxidase: L-lysine-eta-oxidase," Biochimica et Biophysica Acta 1764 (2006) 1577-1585.

Johnson P. et al. "Packaging of chemicals in the defensive secretory glands of the sea hare *Aplysia californica*," Journal of Experimental Biology; 209, pp. 78-88 (2006).

Ko K-C et al. "Identification of Potent Bactericidal Compounds Produced by Escapin, an L-Amino Acid Oxidase in the Ink of the Sea Hare *Aplysia californica*," Antimicrobial Agents and Chemotherapy, Dec. 2008, vol. 52, No. 12 p. 4455-4462.

\* cited by examiner

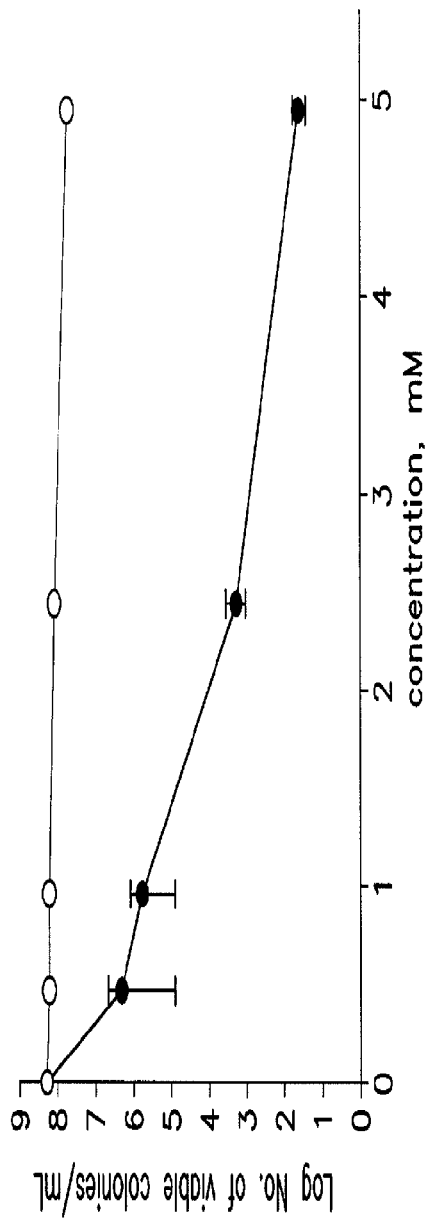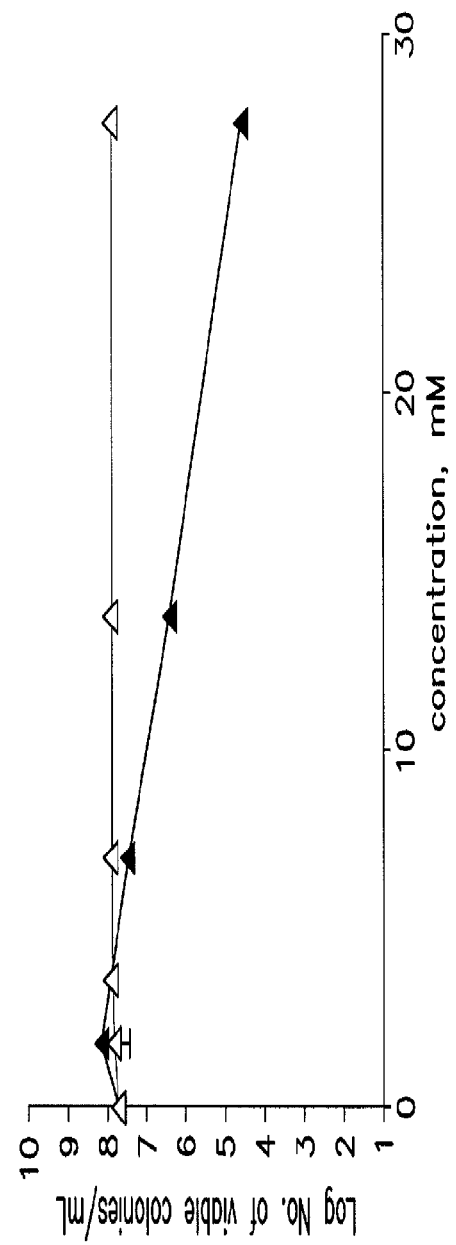

ANTIMICROBIAL COMPOSITIONS AND METHODS OF USE

CROSS REFERENCE TO RELATED APPLICATIONS

This application claims the benefit of priority to U.S. Provisional Application No. 61/083,790 filed Jul. 25, 2008, which is incorporated herein by reference in its entirety.

STATEMENT REGARDING FEDERALLY SPONSORED RESEARCH

This invention was made with government support under the following grants: Grant IBN-061485, IBN-0614685, and MCB-054571 awarded by the National Science foundation, and GM-34766 awarded by the National Institute of Health. The government has certain rights in the invention.

FIELD OF THE DISCLOSURE

Disclosed herein are antimicrobial compositions, kits, and articles of manufacture. Further disclosed herein are methods for treating surfaces, both inert and living, including tissue, inter alia, wounds, with the disclosed compositions.

BACKGROUND OF THE DISCLOSURE

Antimicrobial compositions, i.e., bactericidal or bacteriostatic compositions, typically comprise a single potent ingredient or an admixture of ingredients which act to provide antimicrobial activity. Compositions comprising a single potent ingredient, for example, an organic molecule, may be limited to one species of bacteria or to a limited class of microorganisms. Also, the target microorganisms may develop immunity to a single chemical species.

There is a long felt need for antimicrobial compositions that can be either formulated by the manufacturer or prepared when ready for use by the consumer and which can be used as an antimicrobial found in nature to induce antimicrobial activity and which can serve as an effective method for treating a situs infected by a microorganism.

SUMMARY OF THE DISCLOSURE

Disclosed herein are antimicrobial compositions and methods for using the disclosed compositions. Disclosed compositions comprise:
  a) one or more of the disclosed α-keto acids; and
  b) source of peroxide;
  wherein the composition has a pH of from about 3 to about 8.

Further disclosed are kits comprising the disclosed antimicrobial compositions. Also disclosed are articles of manufacture comprising disclosed antimicrobial compositions.

Disclosed methods comprise contacting a microbial-contaminated situs, for example, a wound with an effective amount of a disclosed composition.

Additional advantages of the disclosure will be set forth in part in the description that follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE FIGURES

FIG. 5 depicts a graph showing the effect of hydrogen peroxide concentration on the log number of viable colonies present per mL when a composition comprising hydrogen peroxide is tested with 6-amino-2-ketohexanoic acid (●) versus without 6-amino-2-ketohexanoic acid (○) against *Vibrio harveyi*.

FIG. 6 depicts a graph showing the effect of α-keto acid concentration on the log number of viable colonies present per mL when a composition comprising 6-amino-2-ketohexanoic acid is tested with hydrogen peroxide (▲) versus without hydrogen peroxide (△) against *Staphylococcus aureus*.

DETAILED DESCRIPTION

Figure 1:
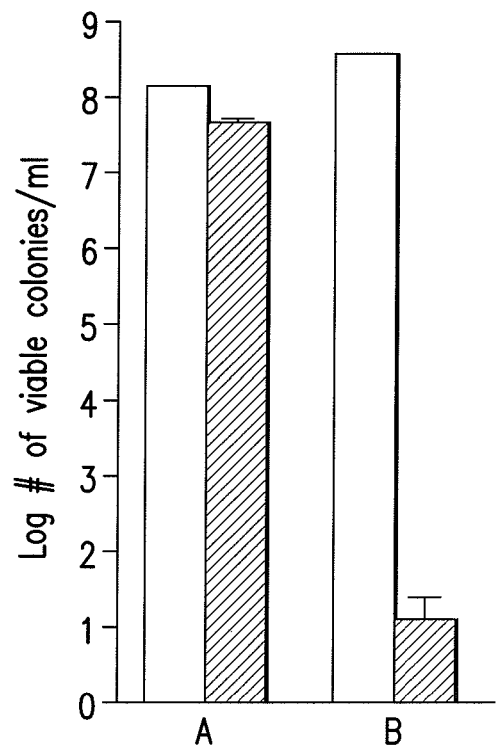
FIG. 1 depicts a graph of the >7 log unit reduction in cell number of a composition comprising 45 mM 6-amino-2-ketohexanoic acid with hydrogen peroxide (B black shading) and without hydrogen peroxide (B white shading) and samples comprising 5-guanidino-2-oxopentanoic acid with hydrogen peroxide (A black shading) and without hydrogen peroxide (A white shading) against *Escherichia coli* MC4100.

The materials, compounds, compositions, articles, and methods described herein may be understood more readily by reference to the following detailed description of specific aspects of the disclosed subject matter and the Examples included therein.

Before the present materials, compounds, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more of the disclosed compounds, the disclosed compounds in combination with other pharmaceutically active compounds, or the disclosed compounds, solvates or diluents of the compounds as defined herein with other pharmaceutically acceptable ingredients.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include any animal, for example, mammals, such as a primate or a human.

By "reduce" or other forms of the word, such as "reducing" or "reduction," is meant lowering of an event or characteristic (e.g., microorganism growth or survival). It is understood that this is typically in relation to some standard or expected value, in other words it is relative, but that it is not always necessary for the standard or relative value to be referred to. For example, "reduces neurodegeneration" means lowering the amount of dopamine producing neurons that are degenerated.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, breakdown, or eliminate a particular characteristic or event (e.g., microorganism growth or survival). The term "control" is used synonymously with the term "treat."

By "sanitizing" or other forms of the word, such as "sanitize" is meant at least a 3 log or greater reduction in the population numbers of undesirable microorganisms. Some of the disclosed compositions are formulated to provide sanitization.

By "disinfecting" or other forms of the word, such as "disinfect" is meant at least a 6 log or greater reduction in the population numbers of undesirable microorganisms. Some of the disclosed compositions are formulated to provide disinfection.

By "sterilizing" or other forms of the word, such as "sterilize" is meant that after treatment there is no measurable level of undesirable microorganisms. Some of the disclosed compositions are formulated to provide sterilization.

By "situs" is meant a location onto which the disclosed compositions are applied, for example, tissue, food surfaces, hard surfaces, porous surfaces, and the like.

By "the final composition" or other forms is meant the composition applied to a situs. For example, for compositions that are in the form of a solid, the final composition is the composition after the carrier has been added and the composition is ready for administration to a situs. For compositions that are liquid concentrates, the final composition is the composition after further dilution.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

The term "ion," as used herein, refers to any molecule, portion of a molecule, cluster of molecules, molecular complex, moiety, or atom that contains a charge (positive, negative, or both (e.g., zwitterions)) or that can be made to contain a charge. Methods for producing a charge in a molecule, portion of a molecule, cluster of molecules, molecular complex, moiety, or atom are disclosed herein and can be accomplished by methods known in the art, e.g., protonation, deprotonation, oxidation, reduction, alkylation, etc.

The term "anion" is a type of ion and is included within the meaning of the term "ion." An "anion" is any molecule, portion of a molecule (e.g., Zwitterion), cluster of molecules, molecular complex, moiety, or atom that contains a net negative charge or that can be made to contain a net negative charge. The term "anion precursor" is used herein to specifically refer to a molecule that can be converted to an anion via a chemical reaction (e.g., deprotonation).

The term "cation" is a type of ion and is included within the meaning of the term "ion." A "cation" is any molecule, portion of a molecule (e.g., Zwitterion), cluster of molecules, molecular complex, moiety, or atom, that contains a net positive charge or that can be made to contain a net positive charge. The term "cation precursor" is used herein to specifically refer to a molecule that can be converted to a cation via a chemical reaction (e.g., protonation or alkylation).

The following chemical hierarchy is used throughout the specification to describe and enable the scope of the present disclosure and to particularly point out and distinctly claim the units which comprise the compounds of the present disclosure, however, unless otherwise specifically defined, the terms used herein are the same as those of the artisan of ordinary skill. The term "hydrocarbyl" stands for any carbon atom-based unit (organic molecule), said units optionally containing one or more organic functional group, including inorganic atom comprising salts, inter alia, carboxylate salts, quaternary ammonium salts. Within the broad meaning of the term "hydrocarbyl" are the classes "acyclic hydrocarbyl" and "cyclic hydrocarbyl" which terms are used to divide hydrocarbyl units into cyclic and non-cyclic classes.

As it relates to the following definitions, "cyclic hydrocarbyl" units can comprise only carbon atoms in the ring (i.e., carbocyclic and aryl rings) or can comprise one or more heteroatoms in the ring (i.e., heterocyclic and heteroaryl rings). For "carbocyclic" rings the lowest number of carbon atoms in a ring are 3 carbon atoms; cyclopropyl. For "aryl" rings the lowest number of carbon atoms in a ring are 6 carbon atoms; phenyl. For "heterocyclic" rings the lowest number of carbon atoms in a ring is 1 carbon atom; diazirinyl. Ethylene oxide comprises 2 carbon atoms and is a $C_2$ heterocycle. For "heteroaryl" rings the lowest number of carbon atoms in a ring is 1 carbon atom; 1,2,3,4-tetrazolyl. The following is a non-limiting description of the terms "acyclic hydrocarbyl" and "cyclic hydrocarbyl" as used herein.

A. Substituted and Unsubstituted Acyclic Hydrocarbyl:

For the purposes of the present disclosure the term "substituted and unsubstituted acyclic hydrocarbyl" encompasses 3 categories of units:

1) linear or branched alkyl, non-limiting examples of which include, methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), and the like; substituted linear or branched alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 3-carboxypropyl ($C_3$), and the like.

2) linear or branched alkenyl, non-limiting examples of which include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.

3) linear or branched alkynyl, non-limiting examples of which include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.

B. Substituted and Unsubstituted Cyclic Hydrocarbyl:

For the purposes of the present disclosure the term "substituted and unsubstituted cyclic hydrocarbyl" encompasses 5 categories of units:

1) The term "carbocyclic" is defined herein as "encompassing rings comprising from 3 to 20 carbon atoms, wherein the atoms which comprise said rings are limited to carbon atoms, and further each ring can be independently substituted with one or more moieties capable of replacing one or more hydrogen atoms." The following are non-limiting examples of "substituted and unsubstituted carbocyclic rings" which encompass the following categories of units:
i) carbocyclic rings having a single substituted or unsubstituted hydrocarbon ring, non-limiting examples of which include, cyclopropyl ($C_3$), 2-methylcyclopropyl ($C_3$), cyclopropenyl ($C_3$), cyclobutyl ($C_4$), 2,3-dihydroxycyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cycloheptyl ($C_7$), cyclooctanyl ($C_8$), 2,5-dimethylcyclopentyl ($C_5$), 3,5-dichlorocyclohexyl ($C_6$), 4-hydroxycyclohexyl ($C_6$), and 3,3,5-trimethylcyclohex-1-yl ($C_6$).
ii) carbocyclic rings having two or more substituted or unsubstituted fused hydrocarbon rings, non-limiting examples of which include, octahydropentalenyl ($C_8$), octahydro-1H-indenyl ($C_9$), 3a,4,5,6,7,7a-hexahydro-3H-inden-4-yl ($C_9$), decahydroazulenyl ($C_{10}$).
iii) carbocyclic rings which are substituted or unsubstituted bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

2) The term "aryl" is defined herein as "units encompassing at least one phenyl or naphthyl ring and wherein there are no heteroaryl or heterocyclic rings fused to the phenyl or naphthyl ring and further each ring can be independently substituted with one or more moieties capable of replacing one or more hydrogen atoms." The following are non-limiting examples of "substituted and unsubstituted aryl rings" which encompass the following categories of units:
i) $C_6$ or $C_{10}$ substituted or unsubstituted aryl rings; phenyl and naphthyl rings whether substituted or unsubstituted, non-limiting examples of which include, phenyl ($C_6$), naphthylen-1-yl ($C_{10}$), naphthylen-2-yl ($C_{10}$), 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyano-naphthylen-1-yl ($C_{10}$).
ii) $C_6$ or $C_{10}$ aryl rings fused with 1 or 2 saturated rings to afford $C_8$-$C_{20}$ ring systems, non-limiting examples of which include, bicyclo[4.2.0]octa-1,3,5-trienyl ($C_8$), and indanyl ($C_9$).

3) The terms "heterocyclic" and/or "heterocycle" are defined herein as "units comprising one or more rings having from 3 to 20 atoms wherein at least one atom in at least one ring is a heteroatom chosen from nitrogen (N), oxygen (O), or sulfur (S), or mixtures of N, O, and S, and wherein further the ring which contains the heteroatom is also not an aromatic ring." The following are non-limiting examples of "substituted and unsubstituted heterocyclic rings" which encompass the following categories of units:
i) heterocyclic units having a single ring containing one or more heteroatoms, non-limiting examples of which include, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), thiazolidinyl ($C_3$), isothiazolinyl ($C_3$), oxathiazolidinonyl ($C_3$), oxazolidinonyl ($C_3$), hydantoinyl ($C_3$), tetrahydrofuranyl ($C_4$), pyrrolidinyl ($C_4$), morpholinyl ($C_4$), piperazinyl ($C_4$), piperidinyl ($C_4$), dihydropyranyl ($C_5$), tetrahydropyranyl ($C_5$), piperidin-2-onyl (valerolactam) ($C_5$), 2,3,4,5-tetrahydro-1H-azepinyl ($C_6$), 2,3-dihydro-1H-indole ($C_8$), and 1,2,3,4-tetrahydroquinoline ($C_9$).
ii) heterocyclic units having 2 or more rings one of which is a heterocyclic ring, non-limiting examples of which include hexahydro-1H-pyrrolizinyl ($C_7$), 3a,4,5,6,7,7a-hexahydro-1H-benzo[d]imidazolyl ($C_7$), 3a,4,5,6,7,7a-hexahydro-1H-indolyl ($C_8$), 1,2,3,4-tetrahydroquinolinyl ($C_9$), and decahydro-1H-cycloocta[b]pyrrolyl ($C_{10}$).

4) The term "heteroaryl" is defined herein as "encompassing one or more rings comprising from 5 to 20 atoms wherein at least one atom in at least one ring is a heteroatom chosen from nitrogen (N), oxygen (O), or sulfur (S), or mixtures of N, O, and S, and wherein further at least one of the rings which comprises a heteroatom is an aromatic ring." The following are non-limiting examples of "substituted and unsubstituted heterocyclic rings" which encompass the following categories of units:
i) heteroaryl rings containing a single ring, non-limiting examples of which include, 1,2,3,4-tetrazolyl ($C_1$), [1,2,3]triazolyl ($C_2$), [1,2,4]triazolyl ($C_2$), triazinyl ($C_3$), thiazolyl ($C_3$), 1H-imidazolyl ($C_3$), oxazolyl ($C_3$), isoxazolyl ($C_3$), isothiazolyl ($C_3$), furanyl ($C_4$), thiophenyl ($C_4$), pyrimidinyl ($C_4$), 2-phenylpyrimidinyl ($C_4$), pyridinyl ($C_5$), 3-methylpyridinyl ($C_5$), and 4-dimethylaminopyridinyl ($C_5$)
ii) heteroaryl rings containing 2 or more fused rings one of which is a heteroaryl ring, non-limiting examples of which include: 7H-purinyl ($C_5$), 9H-purinyl ($C_5$), 6-amino-9H-purinyl ($C_5$), 5H-pyrrolo[3,2-d]pyrimidinyl ($C_6$), 7H-pyrrolo[2,3-d]pyrimidinyl ($C_6$), pyrido[2,3-d]pyrimidinyl ($C_7$), 2-phenylbenzo[d]thiazolyl ($C_7$), 1H-indolyl ($C_8$), 4,5,6,7-tetrahydro-1-H-indolyl ($C_8$), quinoxalinyl ($C_8$), 5-methylquinoxalinyl ($C_8$), quinazolinyl ($C_8$), quinolinyl ($C_9$), 8-hydroxy-quinolinyl ($C_9$), and isoquinolinyl ($C_9$).

5) $C_1$-$C_6$ tethered cyclic hydrocarbyl units (whether carbocyclic units, $C_6$ or $C_{10}$ aryl units, heterocyclic units, or heteroaryl units) which connected to another moiety, unit, or core of the molecule by way of a $C_1$-$C_6$ alkylene unit. Non-limiting examples of tethered cyclic hydrocarbyl units include benzyl $C_1$-($C_6$) having the formula:

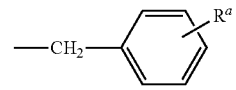

wherein $R^a$ is optionally one or more independently chosen substitutions for hydrogen. Further examples include other aryl units, inter alia, (2-hydroxyphenyl)hexyl $C_6$-($C_6$); naphthalen-2-ylmethyl $C_1$-($C_{10}$), 4-fluorobenzyl ($C_6$), 2-(3-hydroxyphenyl)ethyl $C_2$-($C_6$), as well as substituted and unsubstituted $C_3$-$C_{10}$ alkylenecarbocyclic units, for example, cyclopropylmethyl $C_1$-($C_3$), cyclopentylethyl $C_2$-($C_5$), cyclohexylmethyl $C_1$-($C_6$). Included within this category are substituted and unsubstituted $C_1$-$C_{10}$ alkylene-heteroaryl units, for example a 2-picolyl $C_1$-($C_6$) unit having the formula:

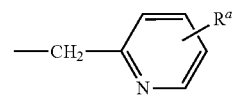

wherein $R^a$ is the same as defined above. In addition, $C_1$-$C_{12}$ tethered cyclic hydrocarbyl units include $C_1$-$C_{10}$ alkyleneheterocyclic units and alkylene-heteroaryl units, non-limiting examples of which include, aziridinylmethyl $C_1$-$(C_2)$ and oxazol-2-ylmethyl $C_1$-$(C_3)$.

For the purposes of the present disclosure carbocyclic rings are from $C_3$ to $C_{20}$; aryl rings are $C_6$ or $C_{10}$; heterocyclic rings are from $C_1$ to $C_9$; and heteroaryl rings are from $C_1$ to $C_9$.

For the purposes of the present disclosure, and to provide consistency in defining the present disclosure, fused ring units, as well as spirocyclic rings, bicyclic rings and the like, which comprise a single heteroatom will be characterized and referred to herein as being encompassed by the cyclic family corresponding to the heteroatom containing ring, although the artisan may have alternative characterizations. For example, 1,2,3,4-tetrahydroquinoline having the formula:

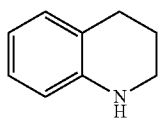

is, for the purposes of the present disclosure, considered a heterocyclic unit. 6,7-Dihydro-5H-cyclopentapyrimidine having the formula:

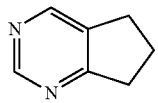

is, for the purposes of the present disclosure, considered a heteroaryl unit. When a fused ring unit contains heteroatoms in both a saturated ring (heterocyclic ring) and an aryl ring (heteroaryl ring), the aryl ring will predominate and determine the type of category to which the ring is assigned herein for the purposes of describing the invention. For example, 1,2,3,4-tetrahydro-[1,8]naphthpyridine having the formula:

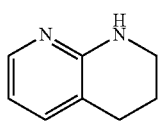

is, for the purposes of the present disclosure, considered a heteroaryl unit.

The term "substituted" is used throughout the specification. The term "substituted" is applied to the units described herein as "substituted unit or moiety is a hydrocarbyl unit or moiety, whether acyclic or cyclic, which has one or more hydrogen atoms replaced by a substituent or several substituents as defined herein below." The units, when substituting for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety, or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain; can have one or more of the hydrogen atoms replaced by a substituent. When a moiety is described as "substituted" any number of the hydrogen atoms may be replaced. For example, 4-hydroxyphenyl is a "substituted aromatic carbocyclic ring (aryl ring)", (N,N-dimethyl-5-amino)octanyl is a "substituted $C_8$ linear alkyl unit, 3-guanidinopropyl is a "substituted $C_3$ linear alkyl unit," and 2-carboxypyridinyl is a "substituted heteroaryl unit."

For the purposes of the present disclosure the terms "compound," "analog," and "composition of matter" stand equally well for each other and are used interchangeably throughout the specification. The disclosed compounds include all enantiomeric forms, diastereomeric forms, salts, and the like.

The compounds disclosed herein include all salt forms, for example, salts of both basic groups, inter alia, amines, as well as salts of acidic groups, inter alia, carboxylic acids. The following are non-limiting examples of anions that can form salts with protonated basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form salts of acidic groups: ammonium, sodium, lithium, potassium, calcium, magnesium, bismuth, lysine, and the like.

It has now been surprisingly discovered that antimicrobial compositions comprising the disclosed α-keto acids and a source of peroxide can form antimicrobial compositions wherein the formed compositions have greater antimicrobial properties than when the components are administered alone or in sequence.

α-Ketoacids

The disclosed compositions comprise one or more α-ketoacids having the formula:

$R^1$ Units $R^1$ is a nitrogen atom comprising unit chosen from:
i) —$NR^{3a}R^{3b}$;
ii) —$NR^4C(=R^5)R^6$;
iii) —$NR^7NR^{8a}R^{8b}$;
iv) —$N=R^9$; or
v) —$C(=NR^{10})R^{11}$.

In one embodiment, $R^1$ is —$NR^{3a}R^{3b}$ wherein $R^{3a}$ and $R^{3b}$ are each independently chosen from:
i) hydrogen;
ii) $C_1$-$C_4$ linear, branched or cyclic alkyl; or
iii) hydroxyl.

In one iteration of this embodiment, $R^{3a}$ and $R^{3b}$ are each hydrogen thereby providing an $R^1$ that has the formula —$NH_2$. Non-limiting examples of α-ketoacids having $R^1$ units equal to —$NH_2$ include:
i) 4-amino-2-oxobutanoic acid and salts thereof having the formula:

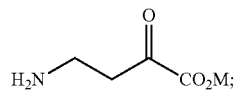

ii) 5-amino-2-oxopentanoic acid and salts thereof having the formula:

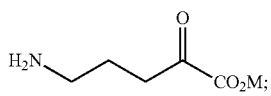

iii) 6-amino-2-oxohexanoic acid and salts thereof having the formula:

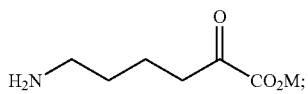

iv) 6-amino-3-methyl-2-oxohexanoic acid and salts thereof having the formula:

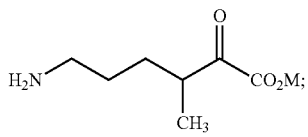

and
v) 6-amino-6-methyl-2-oxohexanoic acid and salts thereof having the formula:

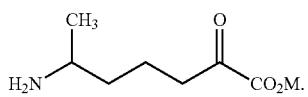

In another iteration of this embodiment, $R^{3a}$ is hydrogen and $R^{3b}$ is $C_1$-$C_4$ alkyl or $R^{3a}$ and $R^{3b}$ are each independently $C_1$-$C_4$ alkyl. Non-limiting examples of this iteration include: methyl 6-(methylamino)-2-oxohexanoate i) 6-(methylamino)-2-oxohexanoic acid and salts thereof having the formula:

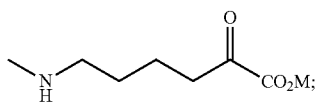

ii) 6-(dimethylamino)-2-oxohexanoic acid and salts thereof having the formula:

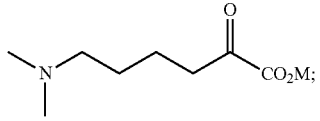

iii) 6-(ethylamino)-2-oxohexanoic acid and salts thereof having the formula:

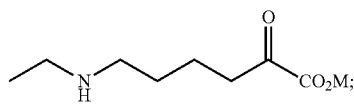

iv) 6-[ethyl(methyl)amino]-2-oxohexanoic acid and salts thereof having the formula:

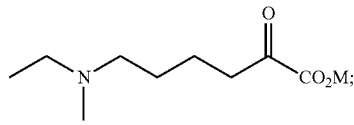

and
v) 6-(diethylamino)-2-oxohexanoic acid and salts thereof having the formula:

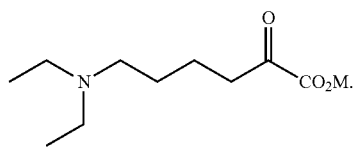

In another embodiment, $R^1$ is —$NR^4C(=R^5)R^6$ wherein
$R^4$ is:
  i) hydrogen; or
  ii) $C_1$-$C_4$ linear, branched or cyclic alkyl.
$R^5$ is:
  i) O;
  ii) S; or
  iii) $NR^{12}$; wherein $R^{12}$ is hydrogen, hydroxyl, or $C_1$-$C_4$ linear, branched or cyclic alkyl.
$R^6$ is:
  i) hydrogen;
  ii) $C_1$-$C_4$ linear, branched or cyclic alkyl;
  iii) $C_1$-$C_4$ linear, branched or cyclic alkoxy; or
  iv) —$NR^{13a}R^{13b}$; wherein $R^{13a}$ and $R^{13b}$ are each independently hydrogen or $C_1$-$C_4$ linear, branched or cyclic alkyl.

In one iteration of this embodiment, $R^4$ is hydrogen, $R^5$ in NH, and $R^6$ is $NH_2$ thereby providing $R^1$ units having the formula is —$NHC(=NH)NH_2$.

In another iteration of this embodiment, $R^4$ is hydrogen, $R^5$ in NH, and $R^6$—$NR^{13a}R^{13b}$; wherein $R^{13a}$ is hydrogen or $C_1$-$C_4$ linear, branched or cyclic alkyl and $R^{13b}$ is $C_1$-$C_4$ linear, branched or cyclic alkyl. Non-limiting examples of this embodiment includes: —$NHC(=NH)NHCH_3$, —$NHC(=NH)N(CH_3)_2$, —$NHC(=NH)NHCH_2CH_3$, and —$NHC(=NH)N(CH_2CH_3)_2$.

In further embodiment, $R^1$ is —$C(=NR^{10})R^{11}$ wherein $R^{10}$ is hydrogen, hydroxyl, or $C_1$-$C_4$ linear, branched or cyclic alkyl; and $R^H$ is chosen from:
  i) $NR^{16}$; wherein $R^{16}$ is hydrogen or $C_1$-$C_4$ linear, branched or cyclic alkyl; or
  ii) $CR^{17a}R^{17b}$; wherein $R^{17a}$ and $R^{17b}$ are each independently chosen from:
    i) hydrogen; or
    ii) $C_1$-$C_4$ linear, branched or cyclic alkyl.

In a still further embodiment, $R^1$ is $—NR^7NR^{8a}R^{8b}$; wherein $R^7$, $R^{8a}$, and $R^{8b}$ are each independently chosen from:
  i) hydrogen; or
  ii) $C_1$-$C_4$ linear, branched or cyclic alkyl.

In a yet further embodiment, $R^1$ is $—N{=}R^9$; wherein $R^9$ is:
  i) $NR^{14}$; or
  ii) $CR^{15a}R^{15b}$; wherein $R^{14}$, $R^{15a}$, and $R^{15b}$ are each independently chosen from:
    i) hydrogen; or
    ii) $C_1$-$C_4$ linear, branched or cyclic alkyl.

$R^{2a}$ and $R^{2b}$ Units $R^{2a}$ and $R^{2b}$ are each independently chosen from:
  i) hydrogen; or
  ii) $C_1$-$C_4$ linear, branched or cyclic alkyl.

The index x is an integer from 1 to 10 and determines the number of units having the formula ($CR^{2a}R^{2b}$) that comprise the disclosed α-ketoacid. The index x can have the values 1, 2, 3, 4, 5, 6, 7, 8, 9, or 10.

M is hydrogen or a water soluble cation in a sufficient amount to provide electronic neutrality. For example, when M is a divalent cation, for example, a $Ca^{2+}$ cation, then two carboxylate moieties will be present. As such, when M is a monovalent cation, for example, a $K^+$ cation, then one carboxylate moiety will be present for each M unit. Non-limiting examples of suitable cations include sodium, lithium, potassium, calcium, magnesium, and bismuth.

The disclosed compositions can comprise from about 0.01% by weight to about 99.99% by weight of one or more disclosed α-keto acids. In one embodiment, the final composition can comprise from about 0.1 mM to about 100 mM of one or more disclosed α-keto acids. In another embodiment, the final composition can comprise from about 2 mM to about 30 mM of one or more disclosed α-keto acids. In a further embodiment, the final composition can comprise from about 10 mM to about 30 mM of one or more disclosed α-keto acids. In a still further embodiment, the final composition can comprise from about 15 mM to about 30 mM of one or more disclosed α-keto acids. In a yet further embodiment, the final composition can comprise from about 20 mM to about 30 mM of one or more disclosed α-keto acids. In a still yet further embodiment, the final composition can comprise from about 25 mM to about 30 mM of one or more disclosed α-keto acids.

The disclosed α-keto acids can be prepared by procedures well known to the artisan of ordinary skill. The following outlines a general synthesis of the disclosed α-keto acids from readily available starting materials.

As in the following example, the formulator can purchase omega nitrogen-containing amino acids, inter alia, ω-amino $C_2$-$C_{11}$ saturated or unsaturated, linear or branched alkyl acids, ω-guanidino $C_2$-$C_{11}$ saturated or unsaturated, linear or branched alkyl acids, ω-amindino $C_2$-$C_{11}$ saturated or unsaturated, linear or branched alkyl acids, and the like as described herein above, and convert the acid to an α-keto acid.

Step (a) Protection of Nitrogen-Containing Group, $R^1$

According to this example, the nitrogen-containing unit $R^1$, unless already protected by a nitrogen protecting group, is converted to a compound having a protected $R^1$ unit, $P^1$.

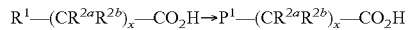

The protecting group, $P^1$, can be any group chosen by the formulator that is compatible with the homologation reaction, step (b) and hydrolysis reaction, step (c).

Step (b) Reaction with a Source of Cyanide.

In step (b) the protected nitrogen-containing acid is reacted with a source of cyanide to form a compound having the general formula:

Any source of cyanide compatible with the above transformation is suitable for use in step (b).

Step (c) Hydrolysis of Cyanide Group.

Step (c) relates to the conversion of the cyaninde moiety to a carboxylate moiety by hydrolysis. The hydrolysis can be accomplished either using an acid or a base depending upon the type of protecting group $P^1$ that is present.

The resulting keto acid can be isolated as the free acid or the acid salt.

Step (d) Removal of Nitrogen-Containing Moiety Protecting Group

Step (d) relates to removal of the protecting group to yield the final α-keto acid as indicated in the reaction below.

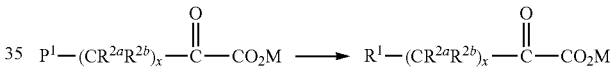

The formulator can use any compatible method for removing the protecting group.

The disclosed α-keto acids can be prepared using the following biochemical procedure. The method of Meister (1952) "Enzymatic preparation of α-keto acids." *J. Biol. Chem.* 197, 309-317 (1952) was slightly modified. For example, 10 mg/mL of L-lysine monohydrochloride was incubated with $3\times10^{-3}$ mg/mL escapin and 0.13 mg/mL catalase in doubly distilled $H_2O$ at 30° C. on a shaker for up to 20-24 hr until L-lysine was completely consumed, as determined by thin layer chromatography. This solution was then filtered using an Amicon Ultra-4 Centrifugal Filter Device (Millipore Corp., Billerica, Mass., USA) to remove escapin and catalase, and then stored at −80° C. until used later. All chemicals were purchased from Sigma-Aldrich (St. Louis, Mo., USA).

Compositions

The disclosed compositions can be fully formulated, i.e., an aqueous solution ready for use, or the disclosed compositions can comprise separate components that are combined by the consumer at the time of use. For example, as disclosed herein, the active ingredients and adjunct materials can be in a dry form that is admixed with water and other carriers at the time of use. Alternatively, the compositions can be impregnated or otherwise disposed upon a substrate and when ready for application to a situs, can be re-constituted by the addition of water.

In one aspect, the disclosed compositions relate to aqueous solutions comprising;
- a) one or more of the disclosed α-keto acids;
- b) one or more sources of peroxide; and
- c) a carrier;

wherein the pH of the composition is from about 3 to about 8.

One embodiment of this aspect relates to compositions comprising:
- a) one or more of the disclosed α-keto acids;
- b) hydrogen peroxide; and
- c) a carrier;

wherein the pH of the composition is from about 3 to about 8.

A general example of this embodiment includes compositions comprising:
- a) from about 2 mM to about 100 mM of one or more of the disclosed α-keto acids;
- b) from about 0.01% by weight (3 mM) to about 30% by weight ($8.8 \times 10^3$ mM) of hydrogen peroxide; and
- c) the balance a carrier;

wherein the pH of the composition is from about 3 to about 8.

Another embodiment of this aspect relates to compositions comprising:
- a) one or more of the disclosed α-keto acids;
- b) hydrogen peroxide;
- c) a buffer system; and
- d) a carrier;

wherein the pH of the composition is from about 3 to about 8.

A general example, of this embodiment includes compositions comprising:
- a) from about 2 mM to about 100 mM of one or more of the disclosed α-keto acids;
- b) from about 0.01% by weight (3 mM) to about 30% by weight ($8.8 \times 10^3$ mM) of hydrogen peroxide;
- c) from about 0.01% to about 50% by weight of a buffer system; and
- d) the balance a carrier;

wherein the pH of the composition is from about 3 to about 8.

A further embodiment of this aspect relates to compositions comprising:
- a) one or more of the disclosed α-keto acids;
- b) hydrogen peroxide;
- c) a stabilizer system; and
- d) a carrier;

wherein the pH of the composition is from about 3 to about 8.

A general example, of this embodiment includes compositions comprising:
- a) from about 2 mM to about 100 mM of one or more of the disclosed α-keto acids;
- b) from about 0.01% by weight (3 mM) to about 30% by weight ($8.8 \times 10^3$ mM) of hydrogen peroxide;
- c) from about 0.01% to about 50% by weight of a stabilizer system; and
- d) the balance a carrier;

wherein the pH of the composition is from about 3 to about 8.

A yet further embodiment of this aspect relates to compositions comprising:
- a) one or more of the disclosed α-keto acids;
- b) hydrogen peroxide;
- c) a buffer system;
- d) a stabilizer system; and
- e) a carrier;

wherein the pH of the composition is from about 3 to about 8.

A general example, of this embodiment includes compositions comprising:
- a) from about 2 mM to about 100 mM of one or more of the disclosed α-keto acids;
- b) from about 0.01% by weight (3 mM) to about 30% by weight ($8.8 \times 10^3$ mM) of hydrogen peroxide;
- c) from about 0.01% to about 50% by weight of a buffer system;
- d) from about 0.01% to about 50% by weight of a stablizer system; and
- e) the balance a carrier;

wherein the pH of the composition is from about 3 to about 8.

In another aspect, the disclosed compositions relate to compositions that can comprise a plurality of components that are admixed at the time of use. The components can be liquid concentrates that are admixed then further diluted prior to use, or the components can be combined prior to use without further dilution with water and/or a suitable carrier.

In this aspect, an application devise can comprise two reservoirs. The first reservoir can contain a solution of the first component and a second reservoir a second component wherein the contents of the two reservoirs are admixed as they are delivered to a situs or within the application devise prior to application to a situs. One embodiment includes a metering device on the apparatus that allows the user to adjust the relative amounts of each component that is delivered to the situs. As such, a greater amount of hydrogen peroxide or the disclosed α-ketoacids can be combined as the user applies the composition.

One embodiment of this aspect comprises:
- A) a first component in the form of a concentrate containing from about 0.01% by weight to about 100% by weight of one or more disclosed α-keto acids; and
- B) a second component containing a source of peroxide, comprising:
  - a) one or more sources of peroxide;
  - b) a stabilizing system; and
  - c) a carrier;

wherein the first component and the second component when combined have a final pH of from about 3 to about 8.

One iteration of this embodiment of compositions comprises:
- A) a first component in the form of a liquid concentrate comprising:
  - a) from about 0.01% by weight to about 90% by weight of one or more disclosed α-keto acids;
  - b) from about 0.01% by weight to about 99.99% by weight of one or more compatible adjunct ingredients; and
  - c) a carrier; and
- B) a second component comprising:
  - a) hydrogen peroxide;
  - b) a stabilizing system; and
  - c) a carrier;

wherein the first component and the second component when combined have a final pH of from about 3 to about 8.

Another iteration of this embodiment of compositions comprises:
A) a first component in the form of a liquid concentrate comprising:
a) from about 0.01% by weight to about 90% by weight of one or more disclosed α-keto acids;
b) from about 0.01% by weight to about 99.99% by weight of a buffer system; and
c) a carrier; and
B) a second component comprising:
a) hydrogen peroxide;
b) a stabilizing system; and
c) a carrier;
wherein the first component and the second component when combined have a final pH of from about 3 to about 8.

A further iteration of this embodiment of compositions comprises:
A) a first component in the form of a liquid concentrate comprising:
a) from about 0.01% by weight to about 90% by weight of one or more disclosed α-keto acids;
b) from about 0.01% by weight to about 99.99% by weight of one or more compatible adjunct ingredients; and
c) a carrier; and
B) a second component comprising:
a) a peroxy acid;
b) a stabilizing system; and
c) a carrier;
wherein the first component and the second component when combined have a final pH of from about 3 to about 8.

A yet further iteration of this embodiment of compositions comprises:
A) a first component in the form of a liquid concentrate comprising:
a) from about 0.01% by weight to about 90% by weight of one or more disclosed α-keto acids;
b) from about 0.01% by weight to about 99.99% by weight of a buffer system; and
c) a carrier; and
B) a second component comprising:
a) peroxy acid;
b) a stabilizing system; and
c) a carrier;
wherein the first component and the second component when combined have a final pH of from about 3 to about 8.

A yet another iteration of this embodiment of compositions comprises:
A) a first component in the form of a liquid concentrate comprising:
a) from about 0.01% by weight to about 90% by weight of one or more disclosed α-keto acids;
b) from about 0.01% by weight to about 99.99% by weight of one or more peroxy acid precursors; and
c) a carrier; and
B) a second component comprising:
a) hydrogen peroxide;
b) a stabilizing system; and
c) a carrier;
wherein the first component and the second component when combined have a final pH of from about 3 to about 8.

Another iteration of this embodiment of compositions comprises:
A) a first component in the form of a liquid concentrate comprising:
a) from about 0.01% by weight to about 90% by weight of one or more disclosed α-keto acids;
b) from about 0.01% by weight to about 99.99% by weight of one or more peroxy acid precursors;
c) from about 0.01% by weight to about 99.99% by weight of a buffer system; and
d) a carrier; and
B) a second component comprising:
a) hydrogen peroxide;
b) a stabilizing system; and
c) a carrier;
wherein the first component and the second component when combined have a final pH of from about 3 to about 8.

In a further aspect, the disclosed compositions relate to compositions that can comprise a plurality of components that are admixed at the time of use wherein the disclosed α-keto acids are a part of a dry first component in the form of a powder, granule, bead, etc. that is either admixed with a carrier prior to combining with the second component or added directly to the second component.

In this aspect, the first component is a solid composition that can be admixed with the second component at the time of use. For example, the composition can be in the form of a kit wherein the composition is reconstituted by admixing the first component and the second component prior to use. The mixing can be done by dissolving a packet or container of the first component in a reservoir containing the second component.

One embodiment of this aspect comprises:
A) a first component in the form of a solid concentrate containing from about 0.01% by weight to about 100% by weight of one or more disclosed α-keto acids; and
B) a second component containing a source of peroxide, comprising:
a) one or more sources of peroxide;
b) a stabilizing system; and
c) a carrier;
wherein the first component and the second component when combined have a final pH of from about 3 to about 8.

One iteration of this embodiment of compositions comprises:
A) a first component in the form of a solid concentrate comprising:
a) from about 0.01% by weight to about 90% by weight of one or more disclosed α-keto acids; and
b) from about 0.01% by weight to about 99.99% by weight of one or more compatible adjunct ingredients; and
B) a second component comprising:
a) hydrogen peroxide;
b) a stabilizing system; and
c) a carrier;
wherein the first component and the second component when combined have a final pH of from about 3 to about 8.

Another iteration of this embodiment of compositions comprises:
A) a first component in the form of a solid concentrate comprising:
a) from about 0.01% by weight to about 90% by weight of one or more disclosed α-keto acids;

b) from about 0.01% by weight to about 99.99% by weight of a buffer system; and
B) a second component comprising:
a) hydrogen peroxide;
b) a stabilizing system; and
c) a carrier;
wherein the first component and the second component when combined have a final pH of from about 3 to about 8.

A further iteration of this embodiment of compositions comprises:
A) a first component in the form of a solid concentrate comprising:
a) from about 0.01% by weight to about 90% by weight of one or more disclosed α-keto acids;
b) from about 0.01% by weight to about 99.99% by weight of one or more compatible adjunct ingredients; and
B) a second component comprising:
a) a peroxy acid;
b) a stabilizing system; and
c) a carrier;
wherein the first component and the second component when combined have a final pH of from about 3 to about 8.

A yet further iteration of this embodiment of compositions comprises:
A) a first component in the form of a solid concentrate comprising:
a) from about 0.01% by weight to about 90% by weight of one or more disclosed α-keto acids;
b) from about 0.01% by weight to about 99.99% by weight of a buffer system; and
B) a second component comprising:
a) peroxy acid;
b) a stabilizing system; and
c) a carrier;
wherein the first component and the second component when combined have a final pH of from about 3 to about 8.

A yet another iteration of this embodiment of compositions comprises:
A) a first component in the form of a solid concentrate comprising:
a) from about 0.01% by weight to about 90% by weight of one or more disclosed α-keto acids;
b) from about 0.01% by weight to about 99.99% by weight of one or more peroxy acid precursors; and
B) a second component comprising:
a) hydrogen peroxide;
b) a stabilizing system; and
c) a carrier;
wherein the first component and the second component when combined have a final pH of from about 3 to about 8.

Another iteration of this embodiment of compositions comprises:
A) a first component in the form of a solid concentrate comprising:
a) from about 0.01% by weight to about 90% by weight of one or more disclosed α-keto acids;
b) from about 0.01% by weight to about 99.99% by weight of one or more peroxy acid precursors;
c) from about 0.01% by weight to about 99.99% by weight of a buffer system; and
B) a second component comprising:
a) hydrogen peroxide;
b) a stabilizing system; and
c) a carrier;
wherein the first component and the second component when combined have a final pH of from about 3 to about 8.

In another aspect, the compositions can comprise a solid composition wherein a source of hydrogen peroxide is added by the user prior to application to a situs. Compositions according to this aspect comprise:
A) a first component in the form of a solid concentrate comprising:
a) from about 0.01% by weight to about 99.99% by weight of one or more disclosed α-keto acids; and
b) from about 0.01% by weight to about 99.99% by weight of a peroxy acid precursor; and
B) a second component provided by the user comprising:
a) a source of hydrogen peroxide; and
b) a carrier;
wherein the first component and the second component are combined prior to use and the composition has a final pH of from about 3 to about 8.

One embodiment of this aspect relates to compositions comprising:
A) a first component in the form of a solid concentrate comprising:
a) from about 0.01% by weight to about 90% by weight of one or more disclosed α-keto acids;
b) from about 0.01% by weight to about 90% by weight of a peroxy acid precursor; and
c) from about 0.01% by weight to about 90% by weight of a buffer system; and
B) a second component provided by the user comprising:
a) a source of hydrogen peroxide; and
b) a carrier;
wherein the first component and the second component are combined prior to use and the composition has a final pH of from about 3 to about 8.

Sources of Peroxide

The disclosed compositions comprise a source of hydrogen peroxide wherein the concentration of hydrogen peroxide is from about 0.5 mM to about 30 mM in the final composition. In another embodiment, the concentration of hydrogen peroxide is from about 0.5 mM to about 7 mM in the final composition. In a further embodiment, the concentration of hydrogen peroxide is from about 1 mM to about 5 mM in the final composition. In still further embodiment, the concentration of hydrogen peroxide is from about 2 mM to about 5 mM in the final composition.

1. Hydrogen Peroxide

The disclosed compositions can comprise hydrogen peroxide as the source of hydrogen peroxide in any concentration from about 0.0017% by weight (0.5 mM) to about 30% by weight ($8.8 \times 10^3$ mM). In one embodiment, the hydrogen peroxide concentration is from about 0.5% by weight to about 5% by weight. In another embodiment, the hydrogen peroxide concentration is from about 0.1% by weight to about 1% by weight. In a yet further embodiment, the hydrogen peroxide concentration is from about 0.1% by weight to about 4% by weight.

In another embodiment of the disclosed compositions, the solid component described herein can be provided in a container or other suitable package and the user can purchase a medical source of hydrogen peroxide, for example, a 3% solution of stabilized hydrogen peroxide from a store or pharmacy and admix an amount of the purchased hydrogen peroxide with the solid component as directed by the directions listed on a kit or on a package containing the disclosed solid component.

2. Peroxyacids

The disclosed antimicrobial compositions can comprise from about 0.01 weight % to about 50 weight % of one or more peroxyacids. In one iteration, the disclosed compositions can comprise from about 0.05 weight % to 5 weight % of one or more peroxyacids. In another iteration, the disclosed compositions can comprise from about 0.05 weight % to 5 weight % of one or more peroxyacids. In a further iteration, the disclosed compositions can comprise from about 0.5 weight % to 10 weight % of one or more peroxyacids. In a yet another iteration, the disclosed compositions can comprise from about 1 weight % to 5 weight % of one or more peroxyacids. In a yet further iteration, the disclosed compositions can comprise from about 0.5 weight % to 2 weight % of one or more peroxyacids. In a still further iteration, the disclosed compositions can comprise from about 5 weight % to 25 weight % of one or more peroxyacids.

When the disclosed compositions comprise a two component system wherein the two components are combined prior to use, the component comprising the peroxy acid can comprise from about 0.01% to about 100% by weight of one or more peroxy acids. In one embodiment wherein the first component is a solid comprising one or more of the disclosed a-keto acids, the first component can comprised from about 0.01% to about 99.99% by weight of one or more carboxylic acids that can form a peroxy acid upon addition of a source of hydrogen peroxide by the user. In one embodiment, wherein the solid component comprises a buffer system, the first component can comprise from about 0.01% to about 90% by weight of a carboxylic acid that can form a peroxy acid upon addition of a source of hydrogen peroxide by the user.

The one or more peroxyacids can be purchased or the peroxyacids can be formed from the corresponding carboxylic acids. In one embodiment, the peroxyacid or combination of peroxyacids are be formed by combining a hydrogen peroxide ($H_2O_2$) solution with the desired amount of a carboxylic acid or carboxylic acid blend. In the case of higher molecular weight fatty acids, a solvent as part of the carrier can be required to fully solubilize the fatty acid. The $H_2O_2$ solution also can be added to previously made peroxyacids such as peroxyacetic acid, peroxyglutaric acid or various peroxy fatty acids to produce the peroxyacid composition admixture. In one iteration, the compositions can comprise from about 1 weight % to about 50 weight % of free hydrogen peroxide. In another iteration, the compositions can comprise from about, 5 weight % to about 25 weight % of hydrogen peroxide.

Suitable $C_1$-$C_{18}$ peroxyacids are peroxyfatty acids, monoperoxy- or diperoxydicarboxylic acids, and peroxy aromatic acids. The $C_2$-$C_{18}$ peroxyacids employed in the present invention may be structurally represented as follows:

$$R^{100}CO_3H$$

wherein $R^{100}$ is a hydrocarbon moiety having from about 1 to 17 carbon atoms (a $C_8$ peroxyacid is generally represented structurally as $C_7CO_3H$). $R^{100}$ can be substituted in the chain, for example, —OH, —$CO_2H$, or the chain can comprise heteroatoms as in the case of alkyether carboxylic acids. $R^{100}$ can be saturated or unsaturated, linear, branched or cyclic alkyl.

Non-limiting examples of suitable $C_2$-$C_{18}$ carboxylic fatty acids which can be reacted with hydrogen peroxide to form peroxyfatty acids include such saturated fatty acids as acetic ($C_2$), propionic ($C_3$), butyric ($C_4$), pentanoic ($C_5$), hexanoic ($C_6$), heptanoic ($C_7$), octanoic ($C_8$), nonanoic ($C_9$), decanoic ($C_{10}$), undecanoic ($C_{11}$), dodecanoic ($C_{12}$), tridecanoic ($C_{13}$), tetradecanoic ($C_{14}$), hexadecanoic ($C_{16}$), and octadecanoic ($C_{18}$). These acids can be derived from both natural and synthetic sources. Natural sources include animal and vegetable fats or oils which should be fully hydrogenated. Synthetic acids can be produced by the oxidation of petroleum wax.

Other suitable acids are the $C_6$-$C_{18}$ peroxyacids derived from the oxidation of dicarboxylic acids and aromatic acids. Suitable dicarboxylic acids include adipic acid ($C_6$) and sebacic acid ($C_{10}$). Examples of a suitable aromatic acid include benzoic acid, phthalic acid, terephthalic acid, hydroxy benzoic acid, etc. These acids can be reacted with hydrogen peroxide to form the peracid form suitable for use in the disclosed compositions. Non-limiting examples include monoperoxy- or diperoxyadipic acid, monoperoxy- or diperoxysebacic acid, and peroxybenzoic acid.

3. Peroxygen Compounds

The disclosed compositions can comprise a suitable peroxygen compound as the source of hydrogen peroxide. The compositions can comprise from about 0.01% by weight to about 30% by weight of one or more peroxygen compounds. In one embodiment, the compositions comprise from about 0.01% by weight to about 30% by weight of one or more peroxygen compounds. In another embodiment, the compositions comprise from about 0.5% by weight to about 5% by weight of one or more peroxygen compounds. In further embodiment, the compositions comprise from about 1% by weight to about 10% by weight of one or more peroxygen compounds. In a still further embodiment, the compositions comprise from about 2% by weight to about 5% by weight of one or more peroxygen compounds. In a yet further embodiment, the compositions comprise from about 0.5% by weight to about 3% by weight of one or more peroxygen compounds.

One category of peroxygen compounds includes the perborates, for example, anhydrous sodium perborate, sodium perborate monohydrate, or sodium perborate tetrahydrate having the nominal formula $NaBO_2H_2O_2 \cdot 3H_2O$. Other examples of peroxygen compounds are sodium percarbonate, sodium perphosphate, sodium persulfate, and urea peroxide.

The formulator can choose between the disclosed and other peroxygen compounds which release hydrogen peroxide depending upon the formulation and the use thereof. For example, sodium perborate monohydrate provides an available oxygen content equivalent to 32% hydrogen peroxide, whereas an equivalent weight of sodium perborate tetrahydrate provides 50% less hydrogen peroxide on a per weight basis.

Adjunct Ingredients

Buffer System

The disclosed compositions have a pH of from about 3 to about 8. In one embodiment the pH is from about 5 to about 7. In another embodiment, the pH is from about 5 to about 6. In a further embodiment, the pH is from about 4.5 to about 5.5. In a further embodiment, the pH is about 5. In a still further embodiment, the pH is about 6. The compositions, however, can have any pH from about 3 to about 8 or any fractional part thereof, for example, a pH of 3, 3.5, 4, 4.5, 5, 5.5, 6, 6.5, 7, 7.5, and 8.

The disclosed compositions can comprise a buffer system to maintain the pH of the compositions whether pre-formulated as a liquid, diluted at the time of use, or whether constituted at the time of use, at a pH of from about 3 to about 8. In one embodiment the pH is from about 5 to about 7. In another embodiment, the pH is from about 5 to about 6. In a further embodiment, the pH is from about 4.5 to about 5.5. In a further embodiment, the pH is about 5. In a still further embodiment, the pH is about 6. The compositions, however, can comprise a buffer system to buffer the pH from about 3 to about 8 or any fractional part thereof, for example, a pH of 3, 3.5, 4, 4.5, 5, 5.5, 6, 6.5, 7, 7.5, and 8.

The formulator, depending upon the level of antimicrobial activity desired, can adjust the pH of the solution to be compatible with the type of microorganism being treated or the situs of application, for example, the skin of a burn victim, an open wound, an inert surface, or a food surface.

Noon-limiting examples of suitable organic acid buffer systems include acetic acid/sodium acetate, glycolic acid/sodium glycolate, lactic acid/sodium lactate, succinic acid/mono sodium succinate, adipic acid/mono sodium adipate, malic acid/mono sodium malate, tartaric acid/mono sodium tartrate, and the like. Non-limiting examples of suitable inorganic buffer systems include phosphate buffer systems.

Surfactant

The disclosed compositions can comprise from about 0.05% to about 0.2% by weight of a surfactant. In further aspect, the disclosed compositions can comprise from about 0.05% to about 0.2% by weight of a non-ionic surfactant. In one embodiment the surfactant has an HLB of from about 10 to about 20. One aspect of the disclosed compositions comprises a surfactant having an HLB of from about 12 to about 18. A further aspect of the disclosed compositions comprises a surfactant having an HLB of from about 13 to about 16. Another embodiment of the disclosed compositions comprise from about 0.1% to about 0.2% by weight of a surfactant.

In one embodiment, the compositions comprise a nonionic surfactant having an HLB of from about 10 to about 20. One aspect of the disclosed compositions comprises a nonionic surfactant having an HLB of from about 12 to about 18. A further aspect of the disclosed compositions comprises a non-ionic surfactant having an HLB of from about 13 to about 16. Another embodiment of the disclosed compositions comprise from about 0.1% to about 0.2% by weight of a nonionic surfactant.

Suitable surfactants include anionic surfactants, for example, linear alkyl sulfates. Non-limiting examples of linear alkyl sulfate surfactants include $C_{10}$ (decyl) sulfate, $C_{12}$ (dodecyl) sulfate, and $C_{14}$ (tetradecyl) sulfate. In addition, mixtures of two or more alkyl surfactants can be used. Suitable salts of linear alkyl sulfates include ammonium, sodium, and potassium.

In addition, branched alkyl surfactants can be used in the disclosed compositions, for example, mid-chain branched alkyl sulfate surfactants as disclosed in U.S. Pat. No. 6,232,282 included herein by reference in its entirety.

Suitable nonionic surfactants for use in the disclosed compositions include polyoxyethylene $C_6$-$C_{12}$ alkylphenyl ethers, polyoxyethylene sorbitan tri-($C_{12}$-$C_{18}$)-alkanoates, polyoxyethylene sorbitan di($C_{12}$-$C_{18}$)-alkanoates, polyoxyethylene sorbitan mono-, di-, and tri-($C_{12}$-$C_{18}$)-alkanoates, and polyoxyethylene $C_{12}$-$C_{20}$ alkyl ethers.

One category of suitable nonionic surfactants for use in the disclosed compositions are the polyoxyethylene $C_6$-$C_{12}$ alkylphenyl ethers having the formula:

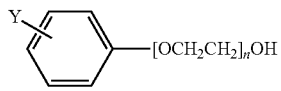

wherein Y is a $C_6$-$C_{12}$ alkyl unit and n is an index from 5 to 40. Non-limiting examples of $C_6$-$C_{12}$ alkylphenyl ethers includes polyoxyethylene(5) isooctylphenyl ethers sold under the tradenames IGEPAL™ CA-520 and IGEPAL™ CO-520, polyoxyethylene(8) isooctylphenyl ethers sold under the tradename TRITON™ X-114, polyoxyethylene(9) nonylphenyl ether sold under the tradename IGEPAL™ CO-630, polyoxyethylene(10) isooctylphenyl ether sold under the tradename TRITON™ X-100, polyoxyethylene(branched) nonylphenyl ethers sold under the tradename TRITON™ N-101, polyoxyethylene(12) nonylphenyl ether sold under the tradename IGEPAL™ CO-720, polyoxyethylene(12) isooctylphenyl ether sold under the tradename IGEPAL™ CA-720, polyoxyethylene(40) nonylphenyl ether sold under the tradename IGEPAL™ CO-890, and polyoxyethylene(40) isooctylphenyl ether sold under the tradename TRITON™ X-405.

Another category of nonionic surfactants for use in the disclosed compositions are polyoxyethylene sorbitan mono-, di-, and tri-($C_{12}$-$C_{18}$)-alkanoates, non-limiting examples of which include polyoxyethylene(20) sorbitan trioleate sold under the tradename TWEEN™ 85, polyoxyethylene(20) sorbitan monooleate sold under the tradename TWEEN™ 80, polyoxy-ethylene(20) sorbitan monostearate sold under the tradename TWEEN™ 60, polyoxyethyl-ene(20) sorbitan monopalmitate sold under the tradename TWEEN™ 40, and polyoxyethyl-ene(20) sorbitan monolaurate sold under the tradename TWEEN™ 20.

A further category of nonionic surfactants for use in the disclosed compositions are polyoxyethylene $C_9$-$C_{20}$ alkyl ethers, non-limiting examples of which include ethoxylate alcohols having the formula:

$$RO(CH_2CH_2O)_mH$$

wherein R is a linear or branched alkyl group having from 6 to 20 carbon atoms and m is an integer of about 2 to about 20. On example of suitable ethoxylate alcohol surfactants are the NEODOL™ ethoxylated alcohols from Shell Chemicals. Non-limiting examples of suitable ethoxylated alcohols include NEODOL™ 91-5, NEODOL™ 91-6, NEODOL™ 91-8, NEODOL™ 91-9, NEODOL™ 23-6.5, NEODOL™ 25-5, NEODOL™ 25-7, NEODOL™ 25-9, NEODOL™ 25-12, NEODOL™ 45-7, and NEODOL™ 135-7, available from BASF.

Peroxy Acid Initiators

For embodiments wherein the disclosed compositions comprise a organic acid in combination with a peroxygen source, i.e. a perborate, wherein the organic acid is converted to a peroxy acid upon formulation, the composition can comprise a preoxy acid activator. In one embodiment, the composition can comprise from about 0.5% by weight to about 15% by weight of an activator. In another embodiment, the composition can comprise more preferably from about 1% by weight to about 10% by weight of an activator.

In one embodiment, the mole ratio organic acid to activator can range from at least 1:1 to about 10:1. In another embodiment, the mole ratio of organic acid to activator can rang from about 3:1 to about 20:1. Non-limiting examples of activators are chosen from tetraacetyl ethylene diamine (TAED), benzoylcaprolactam (BzCL), 4-nitrobenzoylcaprolactam, 3-chlorobenzoyl-caprolactam, benzoyloxybenzenesulphonate (BOBS), nonanoyloxybenzenesulphonate (NOBS), phenyl benzoate (PhBz), decanoyloxybenzenesulphonate ($C_{10}$-OBS), benzoylvalerolactam (BZVL), octanoyloxybenzenesulphonate ($C_8$-OBS), perhydrolyzable esters and mixtures thereof.

Chelating Agents

A variety of chelating agents can be added to the disclosed compositions to enhance biological activity and stability of the compositions comprising peroxy acids. For example, 1-hydroxyethylidene-1,1-diphosphonic acid commercially available from the Monsanto Company under the designation "DEQUEST 2010" has been found to be effective. Other effective chelating agents include 1,6 pyridine dicarboxylic acid. Chelating agents can be added to the disclosed composition to control or sequester hardness ions such as calcium and magnesium. In this manner sanitization capability can be enhanced.

Other materials which are sufficiently stable at the low pH contemplated by the disclosed compositions can be added to the composition to impart desirable qualities depending upon the intended ultimate use. For example, phosphoric acid ($H_3PO_4$) can be added to the composition of the invention to adjust the final pH. Additional compounds can be added to the concentrate (and thus ultimately to the use solution) to change its color or odor, to adjust its viscosity, to enhance its thermal (i.e., freeze-thaw) stability or to provide other qualities which tend to make it more acceptable to the consumer. For solid formulations, anti-caking compounds compatible with the final aqueous solution can be added.

Carrier

The disclosed compositions can comprise a liquid carrier when not in the solid form. The user can add a liquid carrier to a dry or solid formulation to complete the composition, for example, the user in one embodiment will add an amount of water to a powder or other solid formulation. In another embodiment, the user can be directed by the instructions of a kit to add an amount of hydrogen peroxide, for example, a 3% by weight solution of hydrogen peroxide. More than one carrier can be added or more than one carrier can comprise the liquid embodiments disclosed herein.

In one embodiment, water is the carrier. In another embodiment, the carrier can be an aqueous solution of a source of hydrogen peroxide, for example, an aqueous solution of hydrogen peroxide or an aqueous solution of a source of hydrogen peroxide, i.e., a perborate. In addition, $C_1$-$C_{10}$ linear, branched, and cyclic aliphatic alcohols can be either carriers alone or can be a part of the carrier system. In one embodiment, methanol is added as a co-carrier.

Formulations

The disclosed antimicrobial compositions can be formulated to adapt to the method of use. For example, the formulations can be a liquid which is applied directly to the situs to be treated. Alternatively, the formulation can be a two component system, for example, a solid component and a liquid component that are admixed together at the time of use to generate the final antimicrobial composition. In another embodiment, the formulation can comprise two liquids that are admixed to provide the final composition. In a further embodiment, the composition can comprise a solid component in the form of a powder, granule, agglomerate, bead, and the like. The solid component form can be delivered to the situs by any means desired by the formulator, for example, as part of a gel, paste, or powder. In addition, the formulation can be applied to a substrate, for example, a bandage, sanitary napkin, and the like. The formulation can be applied to a substrate as a liquid, allowed to dry, then reconstituted by addition of a liquid carrier or when contacted by a fluid, for example, when wiping down a moist surface such as human skin or when contacted by a body fluid, i.e., fluid from an open wound such as a burn. Solid compositions can comprise all necessary ingredients except the carrier, which when added by the user, provides an effective antimicrobial composition.

The disclosed α-keto acid can be formulated into the disclose compositions in any form or in any manner chosen by the formulator. For example, 6-amino-2-ketohexanoic acid, a disclosed α-keto acid, can be formulated into a composition as the free acid, or as a salt of the acid, for example, as compounds having the formula:

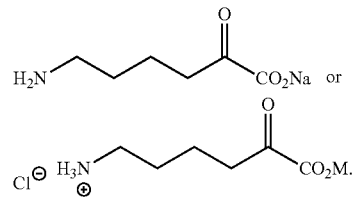

EXAMPLES

The following are non-limiting examples of liquid compositions according to the present disclosure. The amounts listed in the following Tables are number of grams of each ingredient per 1000 mL of solution.

TABLE I

| | EXAMPLES 1-5 | | | | |
|---|---|---|---|---|---|
| Ingredients | 1 | 2 | 3 | 4 | 5 |
| 6-amino-2-ketohexanoic acid | 4 | 4.2 | 4.5 | 5 | 6 |
| hydrogen peroxide* | 0.17 | 0.17 | 0.17 | 0.17 | 0.17 |
| citrate buffer to pH 6 | 5 | 5 | 5 | 5 | 5 |
| ethanol | 2 | 2 | 2 | 2 | 2 |
| water | balance | balance | balance | balance | balance |

*Stabilized with phenacetin

TABLE II

| | EXAMPLES 6-10 | | | | |
|---|---|---|---|---|---|
| Ingredients | 6 | 7 | 8 | 9 | 10 |
| 6-amino-2-ketohexanoic acid | 4 | 4.2 | 4.5 | 5 | 6 |
| hydrogen peroxide* | 0.17 | 0.17 | 0.17 | 0.17 | 0.17 |
| phosphate buffer to pH 6 | 5 | 5 | 5 | 5 | 5 |
| ethanol | 2 | 2 | 2 | 2 | 2 |
| water | balance | balance | balance | balance | balance |

*Stabilized with phenacetin

TABLE II

| | EXAMPLES 11-15 | | | | |
|---|---|---|---|---|---|
| Ingredients | 11 | 12 | 13 | 14 | 15 |
| 6-amino-2-ketohexanoic acid | 4 | 4.2 | 4.5 | 5 | 6 |
| hydrogen peroxide* | 0.25 | 0.25 | 0.25 | 0.25 | 0.25 |
| citrate buffer to pH 6 | 5 | 5 | 5 | 5 | 5 |
| ethanol | 2 | 2 | 2 | 2 | 2 |
| water | balance | balance | balance | balance | balance |

*Stabilized with phenacetin

TABLE IV

EXAMPLES 16-20

| Ingredients | 16 | 17 | 18 | 19 | 20 |
|---|---|---|---|---|---|
| 6-amino-2-ketohexanoic acid | 4 | 4.2 | 4.5 | 5 | 6 |
| hydrogen peroxide* | 0.17 | 0.17 | 0.17 | 0.17 | 0.17 |
| phosphate buffer to pH 6 | 5 | 5 | 5 | 5 | 5 |
| ethanol | 2 | 2 | 2 | 2 | 2 |
| water | balance | balance | balance | balance | balance |

*Stabilized with phenacetin

TABLE V

EXAMPLES 21-25

| Ingredients | 21 | 22 | 23 | 24 | 25 |
|---|---|---|---|---|---|
| 6-amino-2-ketohexanoic acid | 4 | 4.2 | 4.5 | 5 | 6 |
| hydrogen peroxide* | 0.17 | 0.17 | 0.17 | 0.17 | 0.17 |
| citrate buffer to pH 5.5 | 5 | 5 | 5 | 5 | 5 |
| ethanol | 2 | 2 | 2 | 2 | 2 |
| water | balance | balance | balance | balance | balance |

*Stabilized with phenacetin

TABLE VI

EXAMPLES 26-30

| Ingredients | 26 | 27 | 28 | 29 | 30 |
|---|---|---|---|---|---|
| 6-amino-2-ketohexanoic acid | 4 | 4.2 | 4.5 | 5 | 6 |
| hydrogen peroxide* | 0.17 | 0.17 | 0.17 | 0.17 | 0.17 |
| phosphate buffer to pH 5.5 | 5 | 5 | 5 | 5 | 5 |
| ethanol | 2 | 2 | 2 | 2 | 2 |
| water | balance | balance | balance | balance | balance |

*Stabilized with phenacetin

TABLE VII

EXAMPLES 31-35

| Ingredients | 31 | 32 | 33 | 34 | 35 |
|---|---|---|---|---|---|
| 6-amino-2-ketohexanoic acid | 4 | 4.2 | 4.5 | 5 | 6 |
| hydrogen peroxide* | 0.25 | 0.25 | 0.25 | 0.25 | 0.25 |
| citrate buffer to pH 5.5 | 5 | 5 | 5 | 5 | 5 |
| ethanol | 2 | 2 | 2 | 2 | 2 |
| water | balance | balance | balance | balance | balance |

*Stabilized with phenacetin

TABLE VIII

EXAMPLES 36-40

| Ingredients | 36 | 37 | 38 | 39 | 40 |
|---|---|---|---|---|---|
| 6-amino-2-ketohexanoic acid | 4 | 4.2 | 4.5 | 5 | 6 |
| hydrogen peroxide* | 0.17 | 0.17 | 0.17 | 0.17 | 0.17 |
| phosphate buffer to pH 5.5 | 5 | 5 | 5 | 5 | 5 |
| ethanol | 2 | 2 | 2 | 2 | 2 |
| water | balance | balance | balance | balance | balance |

*Stabilized with phenacetin

The composition of Example 1 of Table I can be prepared as follows. A 2-L Erlenmeyer flask is charged with 500 mL of a citric acid/sodium citrate buffer. 6-Amino-2-ketohexanoic acid (4 g, 275 mmol) is dissolved in 2 mL of ethanol. The α-keto acid solution is added to the Erlenmeyer flask with good stirring. Hydrogen peroxide (5.7 mL of a 3% aqueous solution) is added. The volume is made up to 1 liter using distilled water.

The following are non-limiting examples of solid compositions according to the present disclosure. One gram of the compositions disclosed in the following tables are added to 1000 mL of water prior to use. The amounts in the following tables are in grams.

TABLE IX

EXAMPLES 41-45

| Ingredients | 41 | 42 | 43 | 44 | 45 |
|---|---|---|---|---|---|
| sodium 6-amino-2-ketohexanoate | 16.7 | 16.7 | 16.7 | 16.7 | 16.7 |
| sodium perborate tetrahydrate | 7.7 | 7.7 | 7.7 | 7.7 | 7.7 |
| $NaH_2PO_4 \cdot H_2O$ | 29.18 | 48.2 | 60.7 | 66.1 | 68.1 |
| $Na_2HPO_4 \cdot 7H_2O$ | 77.73 | 40.4 | 16.1 | 5.5 | 1.8 |
| NEODOL™ 91-6 | 0.5 | 0.5 | 0.5 | 0.5 | 0.5 |

TABLE X

EXAMPLES 46-50

| Ingredients | 46 | 47 | 48 | 49 | 50 |
|---|---|---|---|---|---|
| sodium 6-amino-2-ketohexanoate | 16.7 | 16.7 | 16.7 | 16.7 | 16.7 |
| sodium perborate tetrahydrate | 15.4 | 15.4 | 15.4 | 15.4 | 15.4 |
| $NaH_2PO_4 \cdot H_2O$ | 29.18 | 48.2 | 60.7 | 66.1 | 68.1 |
| $Na_2HPO_4 \cdot 7H_2O$ | 77.73 | 40.4 | 16.1 | 5.5 | 1.8 |
| NEODOL™ 91-6 | 0.5 | 0.5 | 0.5 | 0.5 | 0.5 |

TABLE XI

EXAMPLES 51-55

| Ingredients | 51 | 52 | 53 | 54 | 55 |
|---|---|---|---|---|---|
| sodium 6-amino-2-ketohexanoate | 8.35 | 8.35 | 8.35 | 8.35 | 8.35 |
| sodium perborate monohydrate | 7.7 | 7.7 | 7.7 | 7.7 | 7.7 |
| $NaH_2PO_4 \cdot H_2O$ | 29.18 | 48.2 | 60.7 | 66.1 | 68.1 |
| $Na_2HPO_4 \cdot 7H_2O$ | 77.73 | 40.4 | 16.1 | 5.5 | 1.8 |
| NEODOL™ 91-6 | 0.5 | 0.5 | 0.5 | 0.5 | 0.5 |

TABLE XII

EXAMPLES 56-50

| Ingredients | 56 | 57 | 58 | 59 | 50 |
|---|---|---|---|---|---|
| sodium 6-amino-2-ketohexanoate | 16.7 | 16.7 | 16.7 | 16.7 | 16.7 |
| sodium perborate monohydrate | 15.4 | 15.4 | 15.4 | 15.4 | 15.4 |
| $NaH_2PO_4 \cdot H_2O$ | 29.18 | 48.2 | 60.7 | 66.1 | 68.1 |
| $Na_2HPO_4 \cdot 7H_2O$ | 77.73 | 40.4 | 16.1 | 5.5 | 1.8 |
| sodium hydrogen succinate | 1.4 | 1.4 | 1.4 | 1.4 | 1.4 |

TABLE XIII

EXAMPLES 61-65

| Ingredients | 61 | 62 | 63 | 64 | 65 |
|---|---|---|---|---|---|
| sodium 6-amino-2-ketohexanoate | 16.7 | 16.7 | 16.7 | 16.7 | 16.7 |
| sodium percarbonate | 6.0 | 6.0 | 6.0 | 6.0 | 6.0 |

TABLE XIII-continued

EXAMPLES 61-65

| Ingredients | 61 | 62 | 63 | 64 | 65 |
|---|---|---|---|---|---|
| $NaH_2PO_4 \cdot H_2O$ | 29.18 | 48.2 | 60.7 | 66.1 | 68.1 |
| $Na_2HPO_4 \cdot 7H_2O$ | 77.73 | 40.4 | 16.1 | 5.5 | 1.8 |
| NEODOL ™ 91-6 | 0.5 | 0.5 | 0.5 | 0.5 | 0.5 |

TABLE XIV

EXAMPLES 66-70

| Ingredients | 66 | 67 | 68 | 69 | 70 |
|---|---|---|---|---|---|
| sodium 6-amino-2-ketohexanoate | 16.7 | 16.7 | 16.7 | 16.7 | 16.7 |
| sodium percarbonate | 6.0 | 6.0 | 6.0 | 6.0 | 6.0 |
| $NaH_2PO_4 \cdot H_2O$ | 29.18 | 48.2 | 60.7 | 66.1 | 68.1 |
| $Na_2HPO_4 \cdot 7H_2O$ | 77.73 | 40.4 | 16.1 | 5.5 | 1.8 |
| NEODOL ™ 91-6 | 0.5 | 0.5 | 0.5 | 0.5 | 0.5 |

The compositions of Examples 1 to 70 can be applied to a substrate. For example, the compositions can be used in medical situations wherein a sterile bandage is to be applied to tissue. A two sided absorbable woven or non-woven cellulosic substrate having a first side and a second side can have deposed upon the first side an effective amount of a composition as disclosed herein. Compositions represented by the non-limiting Examples 1 to 40 can be sprayed on one side of the substrate or alternatively the substrate can be immersed in a solution represented by Examples 1 to 40 and then applied to a wound. In another embodiment, a substrate having a breathable, moisture impermeable topsheet disposed on side two can be used wherein a composition as exemplified in Examples 1 to 70 can be applied to the first side and applied to a wound.

The following tables provide non-limiting examples of the disclosed compositions wherein a solid first component is admixed with a liquid second component at the time of application. For the solid component all values are in grams. For the liquid component all values are weight percent. The volume of the liquid component in each example is 1000 mL.

TABLE XV

| Ingredients | 71 | 72 | 73 | 74 | 75 |
|---|---|---|---|---|---|
| SOLID COMPONENT | | | | | |
| sodium 6-amino-2-ketohexanoate | 16.7 | 16.7 | 16.7 | 16.7 | 16.7 |
| $NaH_2PO_4 \cdot H_2O$ | 29.18 | 48.2 | 60.7 | 66.1 | 68.1 |
| $Na_2HPO_4 \cdot 7H_2O$ | 77.73 | 40.4 | 16.1 | 5.5 | 1.8 |
| LIQUID COMPONENT | | | | | |
| hydrogen peroxide | 5 | 5 | 5 | 5 | 5 |
| phenacetin | 0.05 | 0.05 | 0.05 | 0.05 | 0.05 |
| water | balance | balance | balance | balance | balance |

TABLE XVI

| Ingredients | 76 | 77 | 78 | 79 | 80 |
|---|---|---|---|---|---|
| SOLID COMPONENT | | | | | |
| sodium 6-amino-2-ketohexanoate | 8.4 | 8.4 | 8.4 | 8.4 | 8.4 |
| $NaH_2PO_4 \cdot H_2O$ | 29.18 | 48.2 | 60.7 | 66.1 | 68.1 |
| $Na_2HPO_4 \cdot 7H_2O$ | 77.73 | 40.4 | 16.1 | 5.5 | 1.8 |
| LIQUID COMPONENT | | | | | |
| hydrogen peroxide | 3 | 3 | 3 | 3 | 3 |
| phenacetin | 0.05 | 0.05 | 0.05 | 0.05 | 0.05 |
| water | balance | balance | balance | balance | balance |

Methods

In one aspect, disclosed herein are methods for treating a situs with one or more of the disclosed compositions to provide antimicrobial protection. This method comprises contacting a situs in need of protection against micro organisms with a composition comprising:
  a) one or more of the disclosed α-keto acids;
  b) one or more sources of peroxide; and
  c) a carrier;
wherein the pH of the composition is from about 3 to about 8.

In a further embodiment, this method comprises contacting a situs in need of protection against microorganisms with a composition comprising:
  A) a first component in the form of a concentrate containing from about 0.01% by weight to about 100% by weight of one or more disclosed α-keto acids; and
  B) a second component containing a source of peroxide, comprising:
    a) one or more sources of peroxide;
    b) a stabilizing system; and
    c) a carrier;
wherein the first component and the second component when combined have a final pH of from about 3 to about 8.

In another embodiment, this method comprises contacting a situs in need of protection against micro organisms with a composition comprising:
  A) a first component in the form of a solid concentrate containing from about 0.01% by weight to about 100% by weight of one or more disclosed α-keto acids; and
  B) a second component containing a source of peroxide, comprising:
    a) one or more sources of peroxide;
    b) a stabilizing system; and
    c) a carrier;
wherein the first component and the second component when combined have a final pH of from about 3 to about 8.

In a yet further embodiment, this method comprises contacting a situs in need of protection against micro organisms with a composition comprising:
  A) a first component in the form of a solid concentrate comprising:
    a) from about 0.01% by weight to about 99.99% by weight of one or more disclosed α-keto acids; and
    b) from about 0.01% by weight to about 99.99% by weight of a peroxy acid precursor; and
  B) a second component provided by the user comprising:
    a) a source of hydrogen peroxide; and
    b) a carrier;
wherein the first component and the second component are combined prior to use and the composition has a final pH of from about 3 to about 8.

In another aspect, disclosed herein are methods for sanitizing a situs with one or more of the disclosed compositions to provide sanitation. This method comprises contacting a situs in need of sanitizing with a composition comprising:

a) one or more of the disclosed α-keto acids;
b) one or more sources of peroxide; and
c) a carrier;

wherein the pH of the composition is from about 3 to about 8.

In a further embodiment, this method comprises contacting a situs in need of sanitizing with a composition comprising:
A) a first component in the form of a concentrate containing from about 0.01% by weight to about 100% by weight of one or more disclosed α-keto acids; and
B) a second component containing a source of peroxide, comprising:
a) one or more sources of peroxide;
b) a stabilizing system; and
c) a carrier;

wherein the first component and the second component when combined have a final pH of from about 3 to about 8.

In another embodiment, this method comprises contacting a situs in need of sanitizing with a composition comprising:
A) a first component in the form of a solid concentrate containing from about 0.01% by weight to about 100% by weight of one or more disclosed α-keto acids; and
B) a second component containing a source of peroxide, comprising:
a) one or more sources of peroxide;
b) a stabilizing system; and
c) a carrier;

wherein the first component and the second component when combined have a final pH of from about 3 to about 8.

In a yet further embodiment, this method comprises contacting a situs in need of sanitizing with a composition comprising:
A) a first component in the form of a solid concentrate comprising:
a) from about 0.01% by weight to about 99.99% by weight of one or more disclosed α-keto acids; and
b) from about 0.01% by weight to about 99.99% by weight of a peroxy acid precursor; and
B) a second component provided by the user comprising:
a) a source of hydrogen peroxide; and
b) a carrier;

wherein the first component and the second component are combined prior to use and the composition has a final pH of from about 3 to about 8.

In another aspect, disclosed herein are methods for disinfecting a situs with one or more of the disclosed compositions to provide sanitation. This method comprises contacting a situs in need of disinfecting with a composition comprising:
a) one or more of the disclosed α-keto acids;
b) one or more sources of peroxide; and
c) a carrier;

wherein the pH of the composition is from about 3 to about 8.

In a further embodiment, this method comprises contacting a situs in need of disinfecting with a composition comprising:
A) a first component in the form of a concentrate containing from about 0.01% by weight to about 100% by weight of one or more disclosed α-keto acids; and
B) a second component containing a source of peroxide, comprising:
a) one or more sources of peroxide;
b) a stabilizing system; and
c) a carrier;

wherein the first component and the second component when combined have a final pH of from about 3 to about 8.

In another embodiment, this method comprises contacting a situs in need of disinfecting with a composition comprising:
A) a first component in the form of a solid concentrate containing from about 0.01% by weight to about 100% by weight of one or more disclosed α-keto acids; and
B) a second component containing a source of peroxide, comprising:
a) one or more sources of peroxide;
b) a stabilizing system; and
c) a carrier;

wherein the first component and the second component when combined have a final pH of from about 3 to about 8.

In a yet further embodiment, this method comprises contacting a situs in need of disinfecting with a composition comprising:
A) a first component in the form of a solid concentrate comprising:
a) from about 0.01% by weight to about 99.99% by weight of one or more disclosed α-keto acids; and
b) from about 0.01% by weight to about 99.99% by weight of a peroxy acid precursor; and
B) a second component provided by the user comprising:
a) a source of hydrogen peroxide; and
b) a carrier;

wherein the first component and the second component are combined prior to use and the composition has a final pH of from about 3 to about 8.

In a yet further aspect, disclosed herein are methods for controlling biofilms on a situs with one or more of the disclosed compositions to provide sanitation. This method comprises contacting a situs having one or more biofilms or in need of biofilm formation control with a composition comprising:
a) one or more of the disclosed α-keto acids;
b) one or more sources of peroxide; and
c) a carrier;

wherein the pH of the composition is from about 3 to about 8.

In a further embodiment, this method comprises contacting a situs having one or more biofilms or in need of biofilm formation control with a composition comprising:
A) a first component in the form of a concentrate containing from about 0.01% by weight to about 100% by weight of one or more disclosed α-keto acids; and
B) a second component containing a source of peroxide, comprising:
a) one or more sources of peroxide;
b) a stabilizing system; and
c) a carrier;

wherein the first component and the second component when combined have a final pH of from about 3 to about 8.

In another embodiment, this method comprises contacting a situs having one or more biofilms or in need of biofilm formation control with a composition comprising:
A) a first component in the form of a solid concentrate containing from about 0.01% by weight to about 100% by weight of one or more disclosed α-keto acids; and
B) a second component containing a source of peroxide, comprising:
a) one or more sources of peroxide;
b) a stabilizing system; and
c) a carrier;

wherein the first component and the second component when combined have a final pH of from about 3 to about 8.

In a yet further embodiment, this method comprises contacting a situs having one or more biofilms or in need of biofilm formation control with a composition comprising:

A) a first component in the form of a solid concentrate comprising:
  a) from about 0.01% by weight to about 99.99% by weight of one or more disclosed α-keto acids; and
  b) from about 0.01% by weight to about 99.99% by weight of a peroxy acid precursor; and
B) a second component provided by the user comprising:
  a) a source of hydrogen peroxide; and
  b) a carrier;
wherein the first component and the second component are combined prior to use and the composition has a final pH of from about 3 to about 8.

As it relates to this aspect, the compositions are applied on hard surfaces soiled with hard watermarks, limescale and/or soap scum, and the like. Such soils are frequently encountered on bathroom surfaces.

In one embodiment of the disclosed methods, a composition described above is applied to a situs in a high humidity environment to disrupt biofilms and/or prevent their formation. The situs can be a hard surface, including bathroom surfaces such as a shower, toilet or sink, kitchen surfaces such as a sink or waste disposal, or a fabric surface. Alternatively, composition can be used to treat the insides of high-humidity appliances such as dishwashers, refrigerators, etc. Alternatively, the situs can be another kitchen and/or other surface such as a sponge, cutting board (wood or plastic), or wash cloth. In an alternative embodiment of the disclosure, the composition can be used in laundry applications, e.g., applied to the insides of washing machine tubs and/or bowls. The composition can be applied to a fabric. The composition can reduce malodor, assist in cleaning, and/or prevent mold growth on stored fabrics such as clothing, curtains, or the like, in a humid environment.

In an alternative embodiment, the composition can be used to prevent surface fouling with reduced cleaning and/or reduced use of chlorine in pools, spas, and/or hot tubs. In further alternative embodiment, the composition can be used on an outdoor situs such as siding, roofing, decks, and/or patios to prevent outdoor mold and/or algal growth.

In a still further embodiment, the composition can be used in plant and/or flower care vases and/or aquaria, for example, to provide a longer lasting benefit with less cleaning. In a yet further embodiment, the composition can be used in automobile air conditioning units and other air conditioning units prone to biofilm formation to prevent or treat biofilm formation. In a yet still embodiment, the composition can be used to prevent biofilm formation on home-use water filtration systems (e.g., on filters, housings, and/or delivery lines) and industrial water cooling and/or treatment systems or to prevent biofilm formation by basement molds. The compositions are also suitable for treatment of boats and the removal of microorganisms therefrom.

Medical Indications

In one aspect, the disclosed compositions can be combined with one or more pharmaceutically active ingredients, for example, with an antibiotic. This method comprises contacting a situs with a medical composition comprising:
  I) a composition in any form as disclosed herein; and
  II) an effective amount of a pharmaceutically active ingredient.

The composition may be used to treat a subject for a disease state associated with biofilm development, such as a bacterial infection, for cystic fibrosis or HIV, or for an immunocompromised subject. In another embodiment, the composition can be used as a treatment for medical or dental devices such as catheters, tubing, prostheses, etc. to prevent or treat biofilm formation thereon. In a further embodiment, the composition can be used in oral care applications such as on teeth or dentures to control plaque and/or odor.

In a further aspect, the composition can be used to control biofilm formation on skin, e.g., for dandruff control (prevention of Malassezia biofilms on scalp), in hand/skin sanitizers (prevention of growth or restoration of natural microflora), for deodorant applications, or for foot care (prevention of fungal growth such as Athletes' Foot without disrupting natural microflora). In one embodiment of the invention, the composition can be used in shoe care applications to control bacterial and/or fungal biofilm formation on shoe surfaces. In a further embodiment, the composition can be used to prevent toxic shock syndrome or to restore imbalanced microflora (e.g., occluded skin in for example, diapers, or the vaginal tract).

Other Methods of Use

In a further aspect, the composition can be used in any process machinery having metal, ceramic, glass, composite, or polymer parts, particularly in paper, food, drug, and cosmetic processing applications or can be used to prevent biofilm formation on metal, ceramic, glass, composite, or polymer parts and to prevent growth of fungal or bacterial biofilms in paper products. In one embodiment, the composition can be used as a method for treating food and/or beverages, i.e., as a preservative.

In an alternative embodiment of the invention, the compound and/or composition can be used in generalized surface coatings to prevent biofouling (e.g. paints or coatings for houses, boats, fabrics, carpets, shoes, etc.). In an alternative embodiment of the invention, the compound and/or composition can be used in generalized impregnated materials (e.g. plastics, wood, composites) or controlled delivery systems. In an alternative embodiment of the invention, the compounds and/or compositions can be used in construction applications such as materials protection (e.g., wood, siding, roofs, etc.) and equipment protection. In an alternative embodiment of the invention the compounds and/or compositions can be used in marine and freshwater biofouling prevention (e.g., on boats, docks, jettys, buoys, ropes, and military applications). As noted above, the present composition is useful in the cleaning or sanitizing of processing facilities or equipment in the food service, food processing or health care industries. Examples of process facilities in which the composition of the invention can be employed include a dairy milk line, a continuous brewing system, food processing lines such as pumpable food systems and beverage lines, etc. Food service wares can also be sanitized with the composition of the invention. The composition is also useful in sanitizing or disinfecting solid surfaces such as floors, counters, furniture, medical tools and equipment, etc., found in the health care industry. Such surfaces often become contaminated with liquid body spills such as blood, other hazardous body fluids or mixtures thereof.

Generally, the actual cleaning of the in-place system or other surface (i.e., removal of unwanted offal therein) is accomplished with a different material such as a formulated detergent which is introduced with heated water. After this cleaning step, the instant sanitizing composition would be applied or introduced into the system at a use solution concentration in unheated, ambient temperature water. Although in some embodiments it is not normally necessary to heat the aqueous use solution of the present composition, under some circumstances heating may be desirable to further enhance its antimicrobial activity.

Microorganisms

The following are non-limiting examples of microorganisms that can be treated by the disclosed compositions and methods.

The Gram-positive bacteria treatable by the compositions and methods disclosed herein can include, but are not limited to, *M. tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies *paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides,* and other *Nocardia* species, *Streptococcus viridans* group, *Peptococcus* species, *Peptostreptococcus* species, *Actinomyces israelii* and other *Actinomyces* species, *Propionibacterium acnes,* and *Enterococcus* species. The Gram-negative bacteria treatable by the compositions and methods disclosed herein can include, but are not limited to, *Clostridium tetani, Clostridium perfringens, Clostridium botulinum,* other *Clostridium* species, *Pseudomonas aeruginosa,* other *Pseudomonas* species, *Campylobacter* species, *Vibrio cholerae, Ehrlichia* species, *Actinobacillus pleuropneumoniae, Pasteurella haemolytica, Pasteurella multocida,* other *Pasteurella* species, *Legionella pneumophila,* other *Legionella* species, *Salmonella typhi,* other *Salmonella* species, *Shigella* species *Brucella abortus,* other *Brucella* species, *Chlamydi trachomatis, Chlamydia psittaci, Coxiella burnetti, Escherichia coli, Neiserria meningitidis, Neiserria gonorrhea, Haemophilus influenzae, Haemophilus ducreyi,* other *Hemophilus* species, *Yersinia pestis, Yersinia enterolitica,* other *Yersinia* species, *Escherichia coli, E. hirae* and other *Escherichia* species, as well as other *Enterobacteriacae, Brucella abortus* and other *Brucella* species, *Burkholderia cepacia, Burkholderia pseudomallei, Francisella tularensis, Bacteroides fragilis, Fusobascterium nucleatum, Provetella* species, *Cowdria ruminantium, Klebsiella* species, and *Proteus* species.

The above examples of Gram-positive, Gram-negative bacteria are not intended to be limiting, but are intended to be representative of a larger population including all biofilm-associated bacteria, as well as non-Gram test responsive bacteria. Examples of other species of bacteria include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Globicatella, Gemella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella.*

A situs to be treated, for example, a biofilm, can also contain other microorganisms such as, for example, parasites. Examples of parasites that can be present in biofilms, which can be treated by the compositions and methods disclosed herein, include, but are not limited to, *Toxoplasma gondii, Plasmodium* species such as *Plasmodium falciparum, Plasmodium vivax, Plasmodium malariae,* and other *Plasmodium* species, *Trypanosoma brucei, Trypanosoma cruzi, Leishmania* species such as *Leishmania major, Schistosoma* such as *Schistosoma mansoni* and other *Shistosoma* species, and *Entamoeba histolytica.*

A situs to be treated can further contain fungal species such as, but not limited to, *Candida albicans, Cryptococcus neoformans, Histoplama capsulatum, Aspergillus fumigatus, Coccidiodes immitis, Paracoccidiodes brasiliensis, Blastomyces dermitidis, Pneomocystis carnii, Penicillium marneffi, Alternaria* alternate, and *Fusarium* species, which can be treated by the compositions and methods disclosed herein.

In one aspect, the situs can comprise one or more microorganisms chosen from *Bacillus, Campylobacter, Clostridium, Enterococcus, Escherichia, Fusarium, Listeria, Proprionibacterium, Pseudomonas, Salmonella, Staphylococcus, Streptococcus, Shewanella,* and *Toxoplasma.*

Procedures

The effectiveness of the disclosed compositions was tested against three microorganisms: *Escherichia coli, Vibrio harveyi,* and *Staphylococcus aureus.*

FIG. 1 is a graph showing the greater than 7 log unit reduction at pH 7 in viable *Escherichia coli* MC4100 colonies per mL that remains when treated with a composition comprising 45 mM 6-amino-2-ketohexanoic acid and 10 mM hydrogen peroxide (graph B, black shading) and a composition comprising 45 mM 6-amino-2-ketohexanoic acid without hydrogen peroxide (graph B, white shading). Graph A represents the number of colonies per mL that remain when *Escherichia coli* MC4100 is treated with a composition comprising 45 mM 5-guanidino-2-oxopentanoic acid and 10 mM hydrogen peroxide (graph A, black shading) and a composition comprising 45 mM 5-guanidino-2-oxopentanoic acid without hydrogen peroxide (graph A, white shading). Three samples of each test were run in the assay described herein as Procedure 1.

Procedure 1

*Escherichia coli* MC4100 was incubated until the colonies reached a density of approximately $3\times10^8$ cells/mL in Luria-Bertani medium (LB) at pH 7, and were then transferred to LB at pH 7 or LB with adjusted pH buffer. Bacteria were then treated with 6-amino-2-ketohexanoic acid or 5-guanidino-2-oxopentanoic acid each with or without hydrogen peroxide in a 37° C. Thermomixer (Eppendorf) for 10 minutes. Samples were then serially diluted and plated onto Petri dishes with solid LB medium at pH 7, and incubated overnight at 37° C. Viable cell count was achieved by enumeration of colony forming units with appropriate dilutions. Statistical significance of bactericidal effects was analyzed with ANOVA followed by post-hoc tests, $\alpha=0.05$.

A series of assays were conducted to measure the effects of a-keto acid concentration and hydrogen peroxide concentration. The assay described in Procedure 1 was repeated substituting *Escherichia coli* C921-b2, a non-virulent form of a pathogenic strain of this Gram-negative species; *Vibrio harveyi*, a Gram-negative marine species; and *Staphylococcus aureus*, a Gram-positive and pathogenic species for *Escherichia coli* MC4100.

Figure 2:
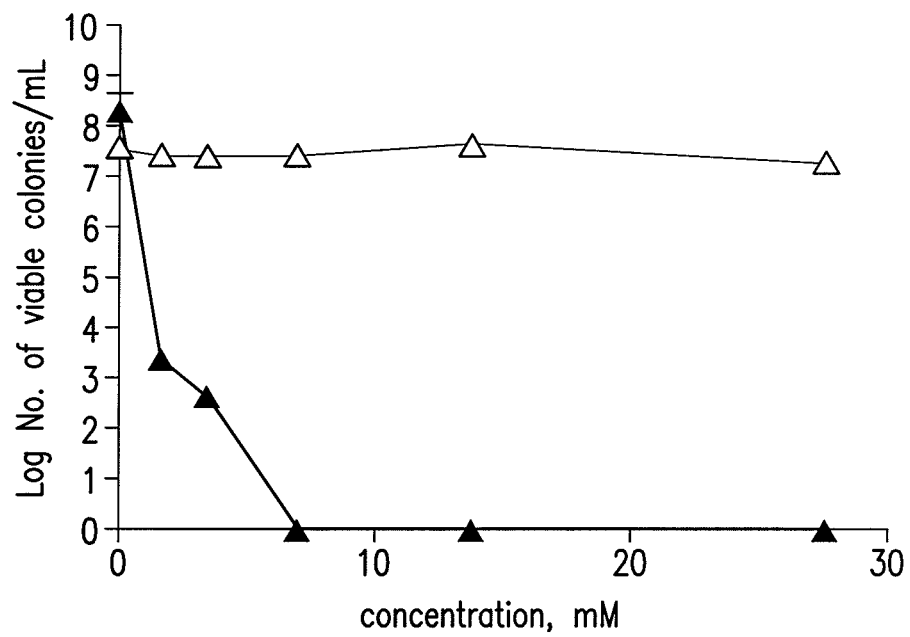
FIG. 2 depicts a graph showing the effect of α-keto acid concentration on the log number of viable colonies present per mL when a composition comprising 6-amino-2-ketohexanoic acid is tested with hydrogen peroxide (▲) versus without hydrogen peroxide (△) against *Escherichia coli* C921-b2.
Figure 4:
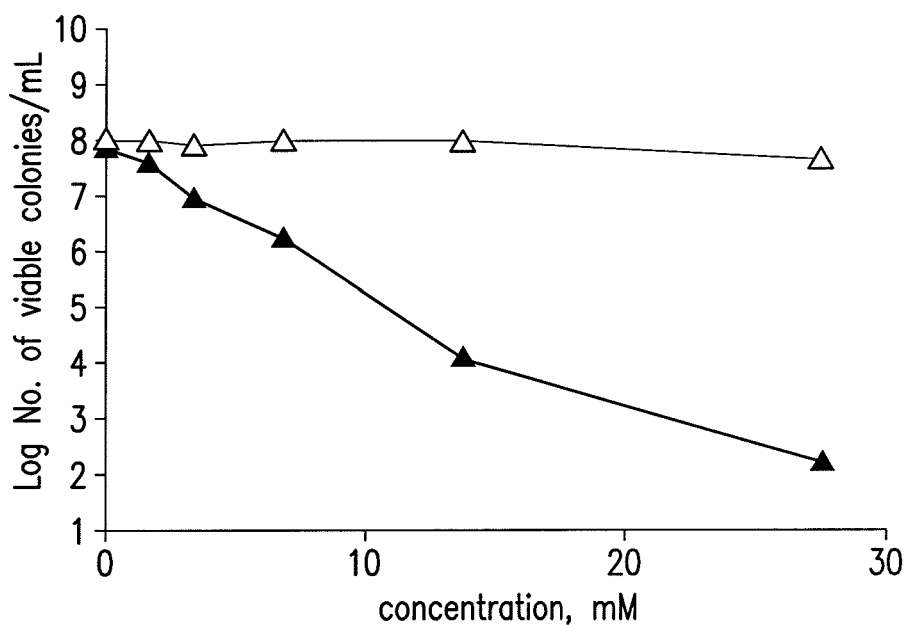
FIG. 4 depicts a graph showing the effect of α-keto acid concentration on the log number of viable colonies present per mL when a composition comprising 6-amino-2-ketohexanoic acid is tested with hydrogen peroxide (▲) versus without hydrogen peroxide (△) against *Vibrio harveyi*.

FIGS. 2, 4 and 6 are graphs representing compositions comprising varying concentrations of 6-amino-2-ketohexanoic acid and 5 mM hydrogen peroxide (▲) versus varying concentrations of 6-amino-2-ketohexanoic acid without hydrogen peroxide (Δ) against *Escherichia coli* C921-b2 (FIG. 2), *Vibrio harveyi* (FIG. 4), and *Staphylococcus aureus* (FIG. 6).

Figure 3:
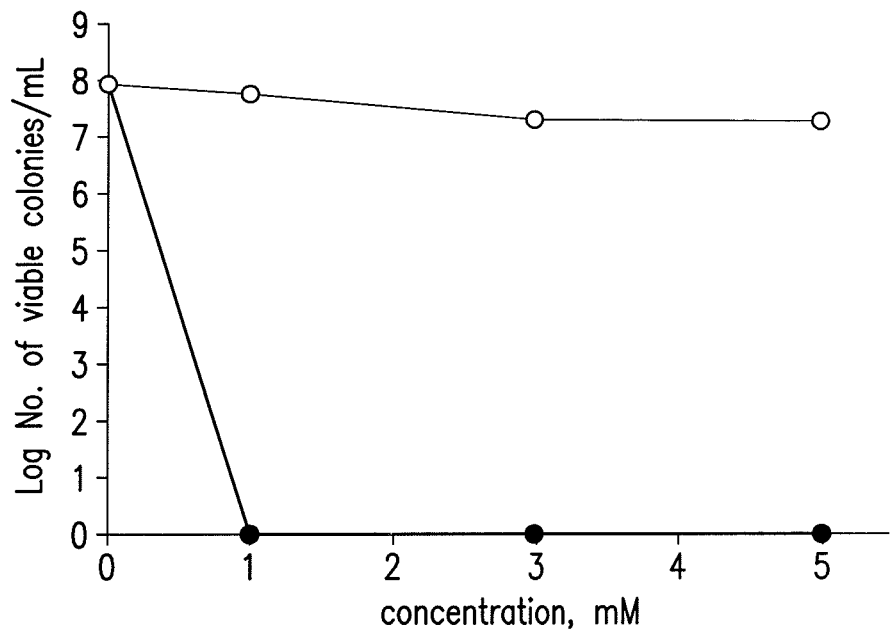
FIG. 3 depicts a graph showing the effect of hydrogen peroxide concentration on the log number of viable colonies present per mL when a composition comprising hydrogen peroxide is tested with 6-amino-2-ketohexanoic acid (●) versus without 6-amino-2-ketohexanoic acid (○) against *Escherichia coli* C921-b2.
Figure 7:
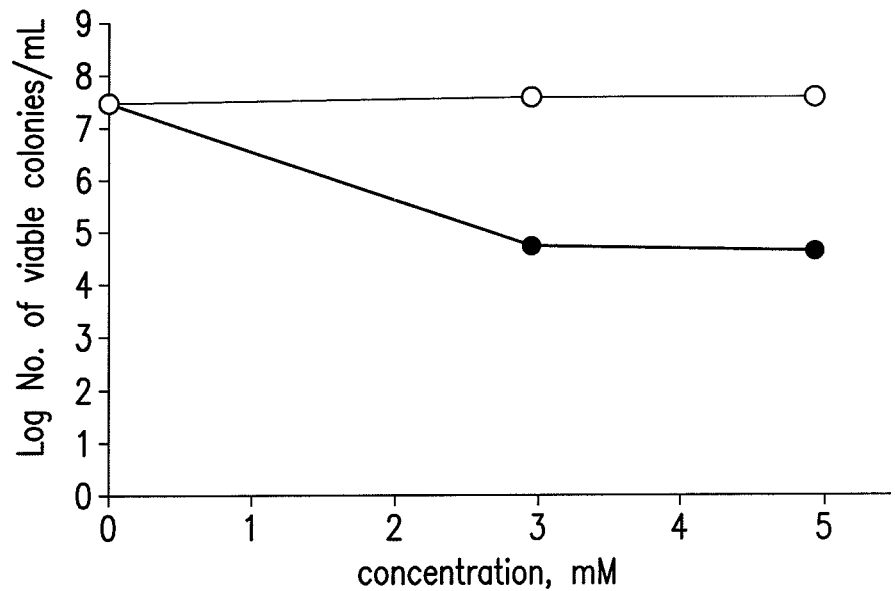
FIG. 7 depicts a graph showing the effect of hydrogen peroxide concentration on the log number of viable colonies present per mL when a composition comprising hydrogen peroxide is tested with 6-amino-2-ketohexanoic acid (●) versus without 6-amino-2-ketohexanoic acid (○) against *Staphylococcus aureus*.

FIGS. 3, 5 and 7 are graphs representing compositions comprising varying concentrations of hydrogen peroxide and 27.5 mM 6-amino-2-ketohexanoic acid (▲) versus varying concentrations of hydrogen peroxide without 6-amino-2-ketohexanoic acid (Δ) against *Escherichia coli* C921-b2 (FIG. 3), *Vibrio harveyi* (FIG. 5), and *Staphylococcus aureus* (FIG. 7).

Figure 8:
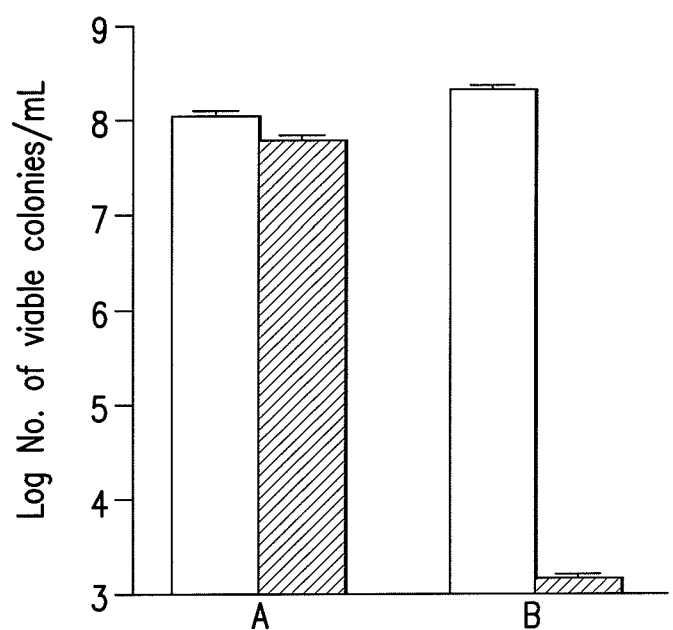
FIG. 8 depicts a graph of the log unit reduction in cell number of a composition comprising 27.5 mM 6-amino-2-ketohexanoic acid with 5 mM hydrogen peroxide (B black shading) and without hydrogen peroxide (B white shading) against *Escherichia coli* MC4100 versus control samples without 6-amino-2-ketohexanoic acid at pH 6.

FIG. 8 depicts a graph of the log unit reduction in cell number of a composition comprising 27.5 mM 6-amino-2-ketohexanoic acid and 5 mM hydrogen peroxide (B black shading) and without hydrogen peroxide (B white shading) against *Escherichia coli* MC4100 versus control samples without 6-amino-2-ketohexanoic acid and hydrogen peroxide (A white shading) and with only 5 mM hydrogen peroxide (A, black shading) at pH 6.

Figure 9:
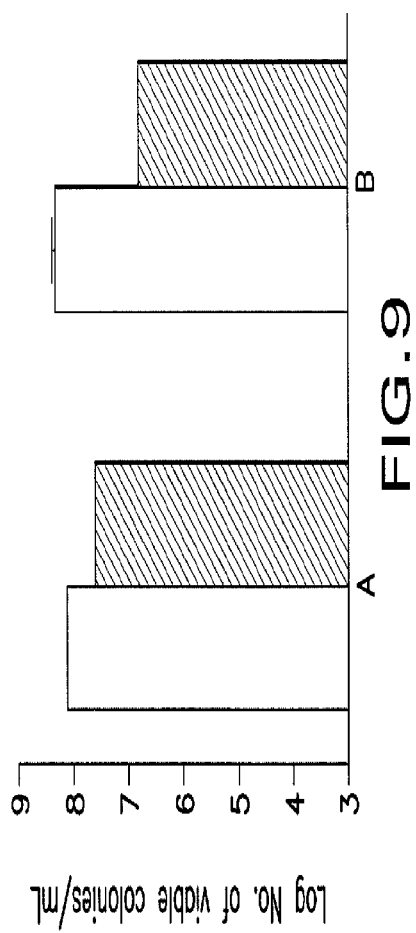
FIG. 9 depicts a graph of the log unit reduction in cell number of a composition comprising 27.5 mM 6-amino-2-ketohexanoic acid with 5 mM hydrogen peroxide (B black shading) and without hydrogen peroxide (B white shading) against *Escherichia coli* MC4100 versus control samples without 6-amino-2-ketohexanoic acid at pH 7.

FIG. 9 depicts a graph of the log unit reduction in cell number of a composition comprising 27.5 mM 6-amino-2-ketohexanoic acid and 5 mM hydrogen peroxide (B black shading) and without hydrogen peroxide (B white shading) against *Escherichia coli* MC4100 versus control samples without 6-amino-2-ketohexanoic acid and hydrogen peroxide (A white shading) and with only 5 mM hydrogen peroxide (A, black shading) at pH 7.

Figure 10:
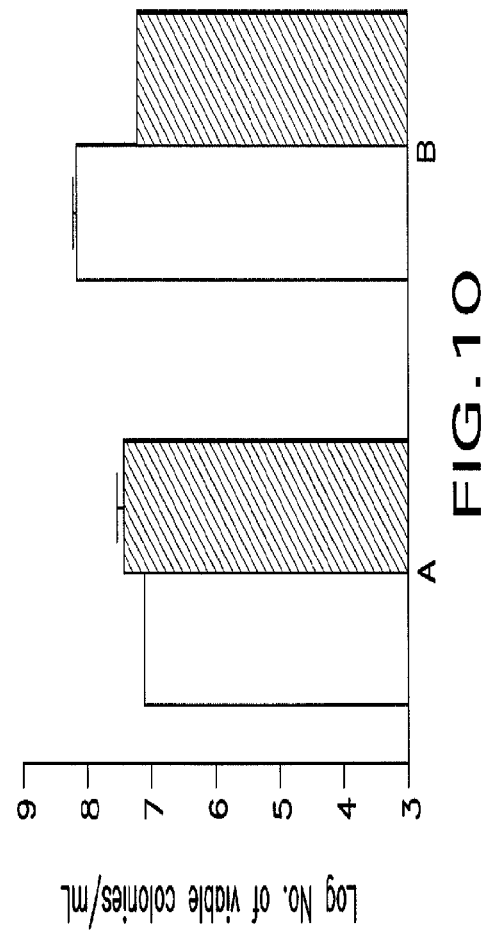
FIG. 10 depicts a graph of the log unit reduction in cell number of a composition comprising 27.5 mM 6-amino-2-ketohexanoic acid with 5 mM hydrogen peroxide (B black shading) and without hydrogen peroxide (B white shading) against *Escherichia coli* MC4100 versus control samples without 6-amino-2-ketohexanoic acid at pH 8.

FIG. 10 depicts a graph of the log unit reduction in cell number of a composition comprising 27.5 mM 6-amino-2-ketohexanoic acid and 5 mM hydrogen peroxide (B black shading) and without hydrogen peroxide (B white shading) against *Escherichia coli* MC4100 versus control samples without 6-amino-2-ketohexanoic acid and hydrogen peroxide (A white shading) and with only 5 mM hydrogen peroxide (A, black shading) at pH 8.

Figure 11:
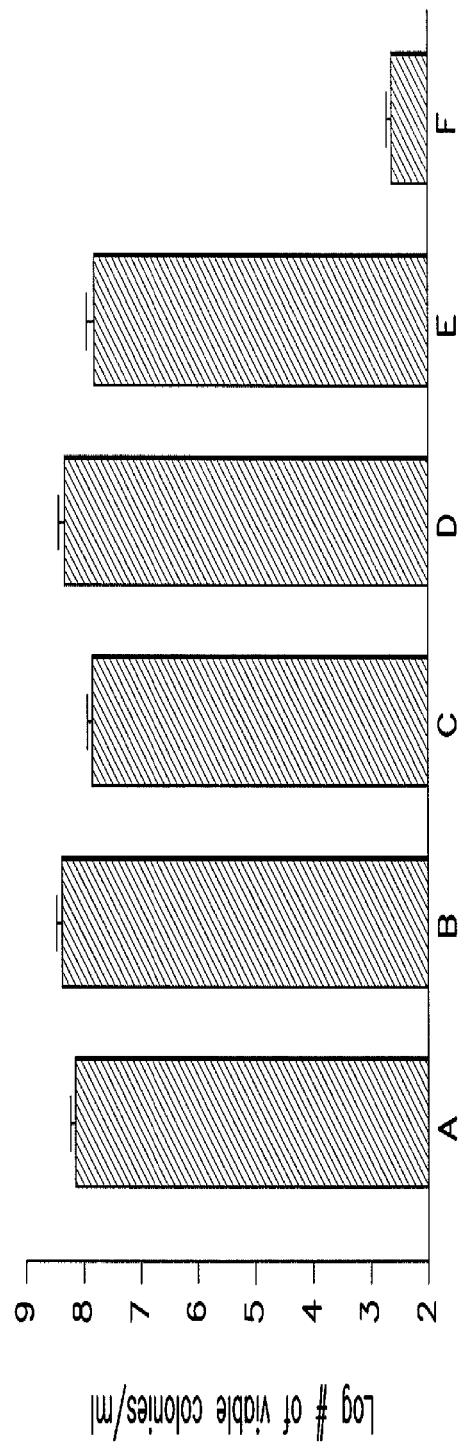
FIG. 11 depicts a graph of the log reduction versus control (A) for serial treatment of the components of the disclosed compositions at pH 7 versus *Escherichia coli* MC4100. Graph (B) represents treatment with 6-amino-2-ketohexanoic acid alone. Graph (C) represents treatment with hydrogen peroxide alone. Graph (D) represents treatment with 6-amino-2-ketohexanoic acid followed by treatment with hydrogen peroxide. Graph (E) represents treatment with hydrogen peroxide followed by 6-amino-2-ketohexanoic acid. Graph (F) represents treatment with an example of the disclosed compositions.

To test the effectiveness of the combination of a disclosed α-keto acid and a source of hydrogen peroxide versus a disclosed α-keto acid alone or a source of hydrogen peroxide alone, Procedure 1 was conducted at pH 7 against *Escherichia coli* MC4100. FIG. 11 depicts a graph of the log reduction versus control (A) for serial treatment of the components of the disclosed compositions at pH 7 versus *Escherichia coli* MC4100. Graph (B) represents treatment with 27.5 mM 6-amino-2-ketohexanoic acid alone. Graph (C) represents treatment with 5 mM hydrogen peroxide alone.

Procedure 1 was then conducted wherein either 27.5 mM 6-amino-2-ketohexanoic acid was added followed by 5 mM hydrogen peroxide or 5 mM hydrogen peroxide was added followed by 27.5 mM 6-amino-2-ketohexanoic acid. Graph (D) represents treatment with 27.5 mM 6-amino-2-ketohexanoic acid followed by treatment with 5 mM hydrogen peroxide. Graph (E) represents treatment with 5 mM hydrogen peroxide followed by 27.5 mM 6-amino-2-ketohexanoic acid. Graph (F) represents treatment with a composition comprising 27.5 mM 6-amino-2-ketohexanoic acid and 5 mM hydrogen peroxide.

Without wishing to be limited by theory, solutions of the disclosed compositions comprise an equilibrium mixture of several transient and/or unstable reactive species. For example, in the case of compositions comprising 6-amino-2-oxohexanoic acid, the following equilibria can occur:

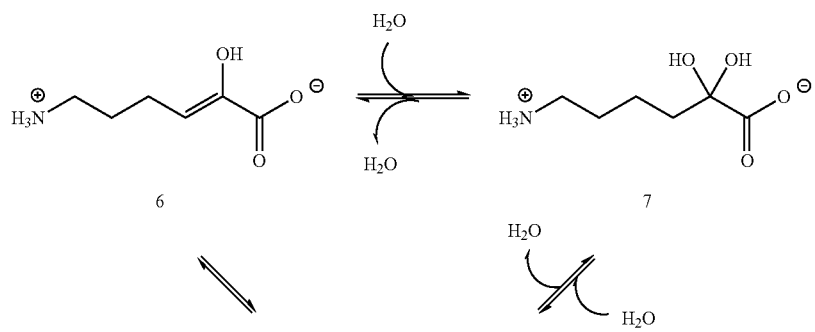

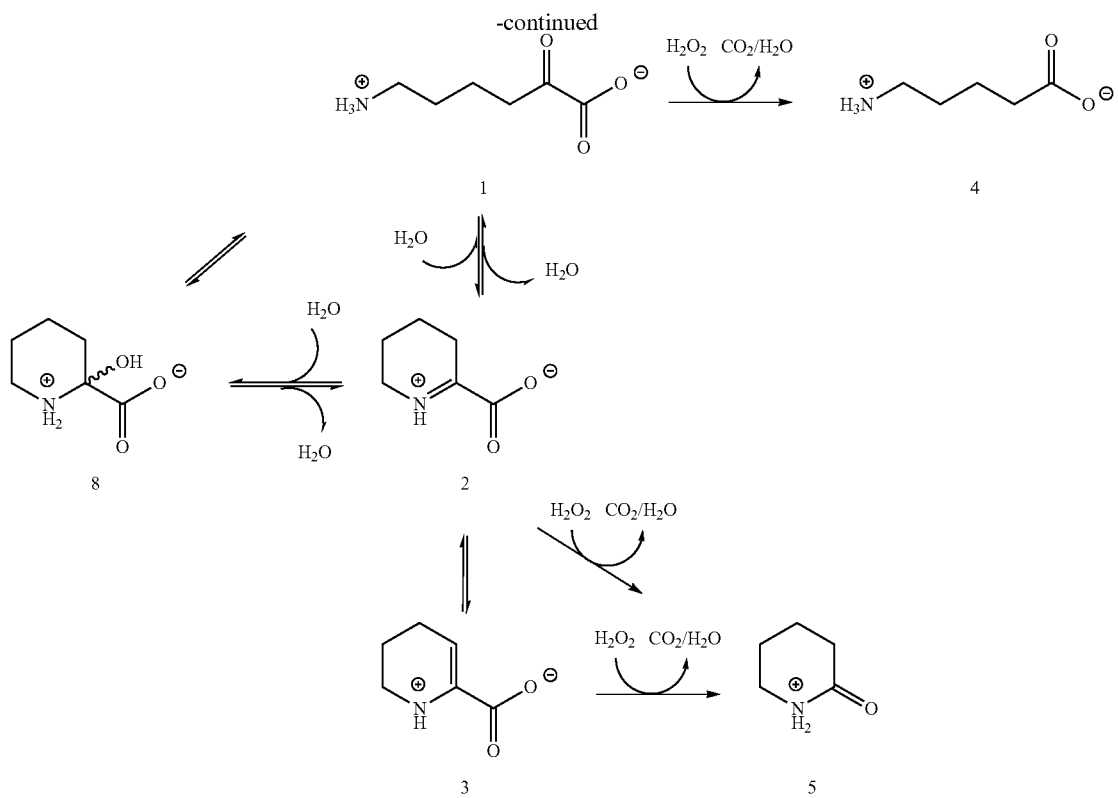

When compounds 4 and 5, which are end products, are combined with a source of hydrogen peroxide, these compounds show no antimicrobial activity. As such, mixtures of intermediates such as those depicted above, are believed to be responsible for the bactericidal activity when the disclosed α-keto acids are applied to a situs in the presence of a source of hydrogen peroxide.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

What is claimed is:

1. An antimicrobial composition, comprising:
   a) 6-amino-2-ketohexanoic acid; and
   b) a source of hydrogen peroxide;
   wherein the composition has a pH of from about 3 to about 8;
   the concentration of 6-amino-2-ketohexanoic acid is from about 15 mM to about 30 mM in the final composition;
   the concentration of the hydrogen peroxide obtained from the source of hydrogen peroxide is from about 0.5 mM to about 10 mM in the final composition; and provided the concentration of the 6-amino-2-ketohexanoic acid and source of hydrogen peroxide are not the same.

2. The composition according to claim 1, wherein the pH is from about 5 to about 7.

3. The composition according to claim 1, wherein the pH is from about 5 to about 6.

4. The composition according to claim 1, wherein the pH is from about 4.5 to about 5.5.

5. The composition according to claim 1, wherein the pH is about 5.

6. The composition according to claim 1, wherein the pH is about 6.

7. The composition according to claim 1, wherein the concentration of 6-amino-2-ketohexanoic acid is from about 20 mM to about 30 mM in the final composition.

8. The composition according to claim 1, wherein the concentration of 6-amino-2-ketohexanoic acid is from about 25 mM to about 30 mM in the final composition.

9. The composition according to claim 1, wherein the concentration of hydrogen peroxide is from about 0.5 mM to about 7 mM in the final composition.

10. The composition according to claim 1, wherein the concentration of hydrogen peroxide is from about 1 mM to about 5 mM in the final composition.

11. The composition according to claim 1, wherein the concentration of hydrogen peroxide is from about 1 mM to about 4 mM in the final composition.

12. The composition according to claim 1, wherein the concentration of hydrogen peroxide is from about 2 mM to about 5 mM in the final composition.

13. A composition according to claim 1, further comprising a surfactant.

14. A composition according to claim 1, further comprising a stabilizer.

15. A composition according to claim 1, further comprising a buffer system.

16. A composition comprising:
A) a first component in the form of a concentrate comprising from about 0.01% by weight to about 90% by weight of 6-amino-2-ketohexanoic acid; and
B) a second component containing a source of hydrogen peroxide, comprising:
   a) from about 0.01% by weight to about 30% by weight of hydrogen peroxide;
   b) from about 0.01% to about 50% by weight of a stabilizing system; and
   c) a carrier;
wherein when components (A) and (B) are combined the concentration of 6-amino-2-ketohexanoic acid is from about 15 mM to about 30 mM in the final composition; and
the concentration of hydrogen peroxide is from about 0.5 mM to about 10 mM in the final composition.

17. The composition according to claim 16, wherein the concentration of 6-amino-2-ketohexanoic acid is from about 20 mM to about 30 mM in the final composition.

18. The composition according to claim 16, wherein the concentration of 6-amino-2-ketohexanoic acid is from about 25 mM to about 30 mM in the final composition.

19. The composition according to claim 16, wherein the concentration of hydrogen peroxide is from about 1 mM to about 5 mM in the final composition.

20. The composition according to claim 16, wherein the concentration of hydrogen peroxide is from about 1 mM to about 4 mM in the final composition.

21. The composition according to claim 16, wherein the concentration of hydrogen peroxide is from about 2 mM to about 5 mM in the final composition.

22. A composition comprising:
A) a first component in the form of a solid concentrate comprising from about 0.01% by weight to about 100% by weight of 6-amino-2-ketohexanoic acid and
B) a second component, comprising:
   a) hydrogen peroxide;
   b) a stabilizing system; and
   c) a carrier;
wherein when components (A) and (B) are combined the concentration of 6-amino-2-ketohexanoic acid is from about 15 mM to about 30 mM in the final composition; and the concentration of hydrogen peroxide is from about 0.5 mM to about 10 mM in the final composition.

23. An antimicrobial composition, comprising:
a) from about 4 g to about 6 g of 6-amino-2-ketohexanoic acid;
b) 5.7 mL of a 3% solution of hydrogen peroxide; and
c) citric acid/sodium citrate buffer;
wherein the composition has a pH about 5.5.

24. An antimicrobial composition, comprising:
a) one or more α-keto acids having the formula:

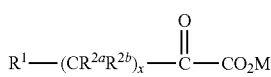

wherein $R^1$ is a nitrogen atom comprising unit chosen from:
i) $-NR^{3a}R^{3b}$;
ii) $-NR^4C(=R^5)R^6$;
iii) $-NR^7NR^{8a}R^{8b}$;
iv) $-N=R^9$; or
v) $-C(=NR^{10})R^{11}$;

$R^{3a}$ and $R^{3b}$ are each independently chosen from:
i) hydrogen;
ii) $C_1$-$C_4$ linear, $C_3$-$C_4$ branched or $C_3$-$C_4$ cyclic alkyl; or
iii) hydroxyl;
$R^4$ is:
i) hydrogen; or
ii) $C_1$-$C_4$ linear, $C_3$-$C_4$ branched or $C_3$-$C_4$ cyclic alkyl;
$R^5$ is:
i) O;
ii) S; or
iii) $NR^{12}$; $R^{12}$ is hydrogen, hydroxyl, or $C_1$-$C_4$ linear, $C_3$-$C_4$ branched or $C_3$-$C_4$ cyclic alkyl;
$R^6$ is:
i) hydrogen;
ii) $C_1$-$C_4$ linear, $C_3$-$C_4$ branched or $C_3$-$C_4$ cyclic alkyl;
iii) $C_1$-$C_4$ linear, $C_3$-$C_4$ branched or $C_3$-$C_4$ cyclic alkoxy; or
iv) $-NR^{13a}R^{13b}$; $R^{13a}$ and $R^{13b}$ are each independently hydrogen or $C_1$-$C_4$ linear, $C_3$-$C_4$ branched or $C_3$-$C_4$ cyclic alkyl;
$R^7$, $R^{8a}$, and $R^{8b}$ are each independently chosen from:
i) hydrogen; or
ii) $C_1$-$C_4$ linear, $C_3$-$C_4$ branched or $C_3$-$C_4$ cyclic alkyl;
$R^9$ is:
i) $NR^{14}$; or
ii) $CR^{15a}R^{15b}$;
$R^{14}$, $R^{15a}$, and $R^{15b}$ are each independently chosen from:
i) hydrogen; or
ii) $C_1$-$C_4$ linear, $C_3$-$C_4$ branched or $C_3$-$C_4$ cyclic alkyl;
$R^{10}$ is hydrogen, hydroxyl, or $C_1$-$C_4$ linear, $C_3$-$C_4$ branched or $C_3$-$C_4$ cyclic alkyl;
$R^{11}$ is chosen from:
i) $NR^{16}$; or
ii) $CR^{17a}R^{17b}$;
$R^{16}$ is hydrogen or $C_1$-$C_4$ linear, $C_3$-$C_4$ branched or $C_3$-$C_4$ cyclic alkyl;
$R^{17a}$ and $R^{17b}$ are each independently chosen from:
i) hydrogen; or
ii) $C_1$-$C_4$ linear, $C_3$-$C_4$ branched or $C_3$-$C_4$ cyclic alkyl;
$R^{2a}$ and $R^{2b}$ are each independently chosen from:
i) hydrogen; or
ii) $C_1$-$C_4$ linear, $C_3$-$C_4$ branched or $C_3$-$C_4$ cyclic alkyl;
the index x is an integer from 1 to 10; and
M is hydrogen or a water soluble cation; and
b) a source of hydrogen peroxide;
wherein the composition has a pH of from about 3 to about 8;
provided the concentration of the one or more α-keto acids and source of hydrogen peroxide are not the same.

25. A method for providing antimicrobial protection to a situs, comprising contacting the situs in need of protection against microorganisms with a composition according to claim 1.

26. A method for sanitizing a situs, comprising contacting the situs with a composition according to claim 1.

27. A method for disinfecting a situs, comprising contacting the situs with a composition according to claim 1.

28. A method for controlling biofilms on a situs, comprising contacting the situs with a composition according to claim 1.

29. A method according to claim 25, wherein the situs is human or animal tissue.

30. A method according to claim 25, wherein the situs is a hard surface.

31. A medical composition comprising a composition according to claim 1 and an effective amount of a pharmaceutically active agent.

* * * * *